US010124025B2

(12) United States Patent
Hsiao et al.

(10) Patent No.: US 10,124,025 B2
(45) Date of Patent: Nov. 13, 2018

(54) COMPOSITIONS AND METHODS COMPRISING BACTERIA FOR IMPROVING BEHAVIOR IN NEURODEVELOPMENTAL DISORDERS

(71) Applicant: California Institute of Technology, Pasadena, CA (US)

(72) Inventors: Elaine Hsiao, Rowland Heights, CA (US); Sara McBride, Pasadena, CA (US); Sarkis K. Mazmanian, Porter Ranch, CA (US); Paul H. Patterson, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 9 days.

(21) Appl. No.: 14/925,242

(22) Filed: Oct. 28, 2015

(65) Prior Publication Data
US 2016/0120920 A1 May 5, 2016

Related U.S. Application Data

(60) Provisional application No. 62/072,873, filed on Oct. 30, 2014.

(51) Int. Cl.
*A61K 35/744* (2015.01)
*A61K 35/74* (2015.01)
*A61K 35/00* (2006.01)

(52) U.S. Cl.
CPC ............ *A61K 35/744* (2013.01); *A61K 35/74* (2013.01); *A61K 2035/115* (2013.01)

(58) Field of Classification Search
CPC .................................................... A61K 35/744
See application file for complete search history.

(56) References Cited

U.S. PATENT DOCUMENTS

| | | | |
|---|---|---|---|
| 5,443,826 A | 8/1995 | Borody | |
| 5,951,977 A | 9/1999 | Nisbet et al. | |
| 7,041,814 B1 | 5/2006 | Weinstock et al. | |
| 7,731,976 B2* | 6/2010 | Cobb | A61K 35/742 424/203.1 |
| 7,749,509 B2* | 7/2010 | Cobb | A61K 35/742 424/203.1 |
| 8,192,733 B2* | 6/2012 | Cobb | A61K 35/742 424/93.1 |
| 9,452,189 B2 | 9/2016 | Mazmanian et al. | |
| 2002/0013270 A1 | 1/2002 | Bolte | |
| 2004/0005304 A1 | 1/2004 | Brudnak | |
| 2004/0028689 A1 | 2/2004 | Borody | |
| 2004/0170617 A1 | 9/2004 | Finegold | |
| 2006/0167057 A1 | 7/2006 | Kong et al. | |
| 2006/0177424 A1* | 8/2006 | Cobb | A61K 35/742 424/93.4 |
| 2007/0280911 A1 | 12/2007 | Cobb et al. | |
| 2009/0118257 A1 | 5/2009 | Jankowski et al. | |
| 2010/0303782 A1* | 12/2010 | Cobb | A61K 35/742 424/93.462 |
| 2011/0081320 A1 | 4/2011 | Westall et al. | |
| 2011/0118135 A1 | 5/2011 | State et al. | |
| 2012/0087895 A1 | 4/2012 | Mazmanian et al. | |
| 2012/0252775 A1 | 4/2012 | Finegold | |
| 2012/0190055 A1 | 7/2012 | Cezar et al. | |
| 2012/0207726 A1 | 8/2012 | Lipkin et al. | |
| 2012/0237482 A1 | 9/2012 | Rodriguez | |
| 2013/0115257 A1 | 5/2013 | Gysemans et al. | |
| 2013/0195802 A1 | 8/2013 | Moore | |
| 2014/0065132 A1 | 3/2014 | Hsiao et al. | |
| 2015/0050246 A1 | 2/2015 | Jones et al. | |
| 2016/0120917 A1 | 5/2016 | Bailey et al. | |
| 2016/0120920 A1 | 5/2016 | Hsiao et al. | |
| 2016/0193256 A1 | 7/2016 | Honda et al. | |
| 2016/0339065 A1 | 11/2016 | Adams et al. | |

FOREIGN PATENT DOCUMENTS

| | | |
|---|---|---|
| CN | 104546932 A | 4/2015 |
| EP | 2 624 863 B1 | 4/2016 |
| EP | 3072524 | 9/2016 |
| JP | 2008-532033 | 8/2008 |
| WO | WO 9611014 | 4/1996 |
| WO | WO 99/19459 | 4/1999 |
| WO | WO 02/07741 | 1/2002 |
| WO | WO 2006/090185 | 8/2006 |
| WO | WO 2006/090185 A1 | 8/2006 |

(Continued)

OTHER PUBLICATIONS

Chi, "Clinical, animal studies probe DISC1's role in autism" Spectrum, Mar. 1, 2010, https://spectrumnews.org/news/clinical-animal-studies-probe-disc1s-role-in-autism/.
Kilpinen, et al., Association of DISC1 with autism and Asperger syndrome' Molecular Psychiatry (2008) 13:187-196.
Penagariko et al., "What does CNTNAP2 reveal about autism spectrum disorder?" Trends in Molecular Medicine (2012) vol. 18, pp. 156-163.
Office Action dated Oct. 7, 2016 in U.S. Appl. No. 14/925,240 filed Oct. 28, 2015.
U.S. Appl. No. 14/925,240, filed Oct. 28, 2015, Hsaio et al.
U.S. Appl. No. 14/925,510, filed Oct. 28, 2015, Bailey et al.
Adams et al. (2011). Gastrointestinal flora and gastrointestinal status in children with autism—comparisons to typical children and correlation with autism severity. BMC Gastroenterol 11, 22.

(Continued)

*Primary Examiner* — Taeyoon Kim
*Assistant Examiner* — Tiffany M Gough
(74) *Attorney, Agent, or Firm* — Knobbe, Martens, Olson & Bear, LLP

(57) ABSTRACT

Some embodiments include bacterial species for use in treatment of one or more autism spectrum disorder (ASD), and/or schizophrenia symptoms in a subject in need thereof. The bacterial species can include *Bacteroides* (e.g., *B. fragilis*, *B. thetaiomtaomicron*, and/or *B. vulgatus*), and/or *Enterococcus* (e.g., *E. faecalis*, *E. faecium*, *E. hirae*, *E. avium*, *E. durans*, *E. gallinarum*, or *E. casseliflavus*). Upon treatment, one or more ASD-related behaviors can be improved in the subject.

19 Claims, 8 Drawing Sheets

(56) References Cited

FOREIGN PATENT DOCUMENTS

| WO | WO2006/110406 | 10/2006 |
|---|---|---|
| WO | WO2009/055362 | 4/2008 |
| WO | WO 2010/056985 | 5/2010 |
| WO | WO2010/056985 A2 | 5/2010 |
| WO | WO 2010/111516 | 9/2010 |
| WO | WO 2011/044516 | 4/2011 |
| WO | WO2011139914 | 11/2011 |
| WO | WO 2012/048152 A2 | 12/2012 |
| WO | WO 2013/154725 | 10/2013 |
| WO | WO 2014/036182 | 3/2014 |
| WO | WO 2014/121301 | 8/2014 |
| WO | WO 2014/121304 | 8/2014 |
| WO | WO 2015/181449 | 12/2015 |
| WO | WO2015/181449 A1 | 12/2015 |
| WO | WO2016/069792 | 5/2016 |
| WO | WO2016/069801 | 5/2016 |
| WO | WO 2016/110768 | 7/2016 |
| WO | WO 2016/110768 A1 | 7/2016 |
| WO | WO 2017/205302 | 11/2017 |
| WO | WO2017/205302 A1 | 11/2017 |
| WO | WO 2017/220708 | 12/2017 |

OTHER PUBLICATIONS

Al-Asmakh et al. (2012). Gut microbial communities modulating brain development and function. Gut Microbes 3, 366-373.
Altieri et al. (2011), Urinary p-cresol is elevated in small children with severe autism spectrum disorder. Biomarkers 16, 252-260.
Amaral et al. (2008). Commensal microbiota is fundamental for the development of Inflammatory pain. Proc Natl Acad Sci U S A 105, 2193-2197.
Amasheh et al. (2009). Na+ absorption defends from paracellular back-leakage by claudin-8 upregulation. Biochem Biophys Res Commun 378, 45-50.
Atladottir, et al. (2010). Maternal infection requiring hospitalization during pregnancy and autism spectrum disorders. J Autism Dev Disord 40, 1423-1430.
Bailey, K.R., and Crawley, J.N. (2009). Anxiety-Related Behaviors in Mice. In Methods of Behavior Analysis in Neuroscience, J.J. Buccafusco, ed. (Boca Raton (FL)).
Bercik et al. (2011). The anxiolytic effect of Bifidobacterium longum NCC3001 involves vagal pathways for gut-brain communication. Neurogastroenterol Motil 23, 1132-1139.
Blumberg, R., and Powrie, F. (2012). Microbiota, disease, and back to health: a metastable journey. Sci Transl Med 4, 137rv137.
Boksa, P. (2010). Effects of prenatal infection on brain development and behavior: a review of findings from animal models. Brain Behav Immun 24, 881-897.
Bourin et al. (2007). Animal models of anxiety in mice. Fundamental & clinical pharmacology 21, 567574.
Bravo et al. (2011). Ingestion of Lactobacillus strain regulates emotional behavior and central Gaba receptor expression in a mouse via the vagus nerve, Proc Natl Acad Sol U S a 108, 16050-16065.
Breiman, L. (2001). Random forests. Mach Learn 45, 5-32.
Brown, et al. (2000). Stress produced by gavage administration in the rat. Contemporary topics in laboratory animal science / American Association for Laboratory Animal Science 39, 17-21.
Bule, et al. (2010). Evaluation, diagnosis, and treatment of gastrointestinal disorders in individuals with ASDs: a consensus report. Pediatrics 125 Suppl 1, S1-18.
Bull et al. (2003). Indolyl-3-acryloyiglycine (IAG) is a putative diagnostic urinary marker for autism spectrum disorders. Med Sci Monit 9, CR422-425.
Burlingham et al. (2003). 34S isotope effect on sulfate ester hydrolysis: mechanistic implications. J Am Chem Soc 125, 13036-13037.
Campbell et al., Bacterial diversity, community structure and potential growth rates along an estuarine salinity gradient, Isme J, (2012).
Canitano, R., and Scandurra, V. (2008). Risperidone in the treatment of behavioral disorders associated with autism in children and adolescents. Neuropsychiatr Dis Treat 4, 723-730.

Caporaso et al. (2010). PyNAST: a flexible tool for aligning sequences to a template alignment. Bioinformatics 26, 266-267.
Caporaso et al. (2010). QIIME allows analysis of high-throughput community sequencing data. Nat Methods 7, 335-336.
CDC (2012). Prevalence of autism spectrum disorders—autism and developmental disabilities monitoring network, 14 sites, United States 2008: MMWR Surveill Summ 61, 1-19.
Clemente et al. (2012). The Impact of the gut microbiota on human health: an integrative view. Cell 148, 1258-1270.
Cohen-Poradosu et al. (2011). Bacteroldes fragills-stimulated interleukin-10 contains expanding disease. The Journal of infectious diseases 204, 363-371.
Collins et al. (2012). The interplay between the intestinal microbiota and the brain. Nat Rev Microbiol 10, 735-742.
Coury, et al. (2012). Gastrointestinal conditions in children with autism spectrum disorder: developing a research agenda. Pediatrics 130 Suppl 2, S160-168.
Critchfield, et al. (2011). The potential role of probiotics in the management of childhood autism spectrum disorders. Gastroenterology research and practice 2011, 161358.
Cryan, J.F., and Dinan, T.G. (2012). Mind-altering microorganisms: the impact of the gut microbiota on brain and behaviour. Nat Rev Neurosci 13, 701-712.
de Hoon et al. (2004). Open source clustering software. Bioinformatics 20, 1453-1454.
de Magistris et al. (2010). Alterations of the intestinal barrier in patients with autism spectrum disorders and in their first-degree relatives. J Pedlatr Gastroenterol Nutr 51, 418-424.
Desbonnet, et al. (2013). Microbiota is essential for social development in the mouse. Molecular psychiatry.
D'Eufemia, et al. (1996). Abnormal intestinal permeability in children with autism. Acta Paediatr 85, 1076-1079.
Edgar, et al. (2011). UCHIME improves sensitivity and speed of chimera detection. Bioinformatics 27, 2194-2200.
Edgar, R.C. (2010). Search and clustering orders of magnitude faster than BLAST. Bioinformatics 26, 2460-2461.
Ewaschuk, et al. (2008). Secreted bioactive factors from Bifidobacterium infantis enhance epithelial cell barrier function. Am J Physlol Gastrointest Liver Physiol 295, G1025-1034.
Extended European Search Report dated Mar. 3, 2014 for European Patent Application No. 11831629.8 filed Oct. 6, 2011.
Faith, D.P. (1992). Conservation Evaluation and Phylogenetic Diversity. Biol Consery 61, 1-10.
Finegold, et al. (2002). Gastrointestinal microflora studies in late-onset autism. Clin Infect Dis 35, S6-S16.
Finegold, et al. (2010). Pyrosequencing study of fecal microflora of autistic and control children. Anaerobe 16, 444-453.
Finegold, et al. (2012). Microbiology of regressive autism, Anaerobe 18, 260-262.
Finegold, S.M. (2011). Desulfovibrio species are potentially important in regressive autism. Medical hypotheses 77, 270-274.
Frye, et al. (2013). Unique acyl-carnitine profiles are potential biomarkers for acquired mitochondrial disease in autism spectrum disorder. Translational psychiatry 3, e220.
Ganapathy et al., "Endogenous Elevation of Homocysteine Induces Retinal Neuron Death in the Cystathionine-Beta-Synthenase Mutant Mouse," Invest. Opthamol. Vis. Sci., 50(9):4460-4470 (2009).
Geyer, M.A., and Swerdlow, H.R. (2001). Measurement of startle response, prepulse inhibition, and habituation. Curr Protoc Neurosci Chapter 8, Unit 8 7.
Gondalia, et al. (2012). Molecular characterisation of gastrointestinal microbiota of children with autism (with and without gastrointestinal dysfunction) and their neurotypical siblings. Autism Res 5, 419-427.
Gorrindo, et al. (2012). Gastrointestinal dysfunction in autism: parental report, clinical evaluation, and associated factors. Autism Res 5, 101-108.
Gorrindo, et al. (2013). Enrichment of elevated plasma f2t-isoprostane levels in individuals with autism who are stratified by presence of gastrointestinal dysfunction. PLoS One 8, e68444.
Grenham, G. Clarke, J. F. Cryan, T. G. Dinan, Brain-gut-microbe communication in health and disease, Front Physiol 2, 94 (Dec. 7, 2011).

(56) References Cited

OTHER PUBLICATIONS

Grimes, A.J, (1959). Synthesis of 35S-labelled arylsulphates by intact animals and by tissue preparations, with particular reference to I-tyrosine 0-sulphate, Biochem J 73, 723.
Grimsley, et al. (2011). Development of social vocalizations in mice. PloS one 6, e17460.
Gulati et al., Mouse Background Strain Profoundly Influences Paneth Cell Function and Intestinal Microbial Composition, PLoS One 7, e32403 (2012).
Hallmayer, et al. (2011). Genetic heritability and shared environmental factors among twin pairs with autism. Arch Gen Psychiatry 68, 1095-1102.
Hammock et al., "2003 Progress Report: Environmental Factors in the Etiology of Autism: Analytic Biomarkers (xenobiotic) Core," Extramural Research, United States Environmental Protection Agency (2003), retrieved online from EPA. <http://cfpub.epa.gov/ncer_abstracts/index.cfm/fuseaction/display.abstractDetail/abstract/7872/report/2003>.
Han, et al. (2012). Autistic-like behaviour in Scn1a+/-31 mice and rescue by enhanced GABA-mediated neurotransmission. Nature 489, 385-390.
Hansen et al. The colitis-associated transcriptional profile of commensal Bacteroides thetaiotaomicron enhances adaptive immune responses to a bacterial antigen. PLoS One. 2012;7(8):e42645, doi: 10.1371/journal.pone.0042645, Epub Aug 3, 2012.
Heijtz, et al. (2011). Normal gut microbiota modulates brain development and behavior. Proc Natl Acad Sci U S A 108, 3047-3052.
Hering, et al. (2012). Determinants of colonic barrier function in inflammatory bowel disease and potential therapeutics. The Journal of physiology 590, 1035-1044.
Holmes, et al. (2006). Claudin profiling in the mouse during postnatal intestinal development and along the gastrointestinal tract reveals complex expression patterns. Gene Expr Patterns 6, 581-588.
Hooper, et al. (2012). Interactions between the microbiota and the immune system. Science 336, 1268-1273.
Horvath, K., and Perman, J.A. (2002). Autism and gastrointestinal symptoms, Curr Gastroenterol Rep 4, 251-258.
Hsiao et al "Microbiota modulate behavioral and physiological abnormalities associated with neurodevelopmental disorders," Cell, vol. 155, No. 7, Dec. 1, 2013.
Hsiao, E.Y., and Patterson, P.H. (2011). Activation of the maternal immune system induces endocrine changes in the placenta via IL-6. Brain Behav Immun 26, 604-616.
Hsiao, et al. (2012). Modeling an autism risk factor in mice leads to permanent immune dysregulation. Proc Natl Acad Sci U S A 109, 12776-12781.
Huang, et al. (2011). The human commensal Bacteroides fragilis binds intestinal mucin. Anaerobe 17, 137-141.
Ibrahim, et al. (2009). Incidence of gastrointestinal symptoms in children with autism: a population-based study. Pediatrics 124, 680-686.
International Search Report and Written Opinion dated Feb. 27, 2012 for International Application PCT/US2011/055159, filed Oct. 6, 2011.
International Search Report and Written Opinion dated Jan. 12, 2016 in International Application No. PCT/US15/57888.
International Search Report and Written Opinion dated Jan. 12, 2016 in International Application No. PCT/US15/57897.
International Search Report dated Feb. 28, 2014 for International Patent Application No. PCT/US2013/057148 filed Aug. 28, 2013.
Kang, et al. (2013). Reduced Incidence of Prevotella and Other Fermenters in Intestinal Microflora of Autistic Children. PLoS One 8, e68322.
Kau, et al, (2011). Human nutrition, the gut microbiome and the immune system. Nature 474, 327-336.
Keszthelyl, et al. (2009). Understanding the role of tryptophan and serotonin metabolism in gastrointestinal function. Neurogastroenterol Motil 21, 1239-1249.
Kidd, Autism, an extreme challege to integrative medicine. Part 2: medical management. Altem. Med. Rev. vol. 7, No. 6, pp. 472-499 (2002).
Knights, et al. (2011). Supervised classification of human microbiota. FEMS microbiology reviews 35, 343-359.
Koenig, et al. (2011). Succession of microbial consortia in the developing infant gut microbiome, Proc Natl Acad Sci U S A 108 Suppl 1, 4678-4585.
Kohane, et al. (2012). The co-morbidity burden of children and young adults with autism spectrum disorders. PLoS One 7, e33224.
Korosi, et al. (2012). Early-life stress mediated modulation of adult neurogenesis and behavior. Behav Brain Res 227, 400-409.
Kursa, M.B., and Rudnickl, W.R. (2010). Feature Selection with the Boruta Package. J Stat Softw 36, 1-13.
Lafaye, et al. (2004). Profiling of sulfoconjugates in urine by using precursor ion and neutral loss scans in tandem mass spectrometry. Application to the Investigation of heavy metal toxicity in rats. J Mass Spectrom 39, 655-664.
Lazio, S.E. (2013), Comment on "Stress in puberty unmasks latent neuropathological consequences of prenatal immune activation in mice." Science 340, 811; discussion 811.
Leatham, et al, (2009). Precolonized human commensal *Escherichia coil* strains serve as a barrier to *E. coil* O157:H7 growth in the streptomycin-treated mouse Intestine, Infect Immun 77, 2876-2886.
Lee et al., in International Meeting for Autism Research (Toronto, Canada, May 17-19, 2012).
Lee, A., and Gemmell, E. (1972). Changes in the mouse intestinal microflora during weaning: role of volatile fatty acids. Infect Immun 5, 1-7.
Lozupone, C., and Knight, R. (2005). UniFrac: a new phylogenetic method for comparing microbial communities. Appl Environ Microblol 71, 8228-8235.
Ludwig, et al. (2004). ARB: a software environment for sequence data. Nucleic Acids Res 32, 1363-1371.
MacFabe, D.F. (2012), Short-chain fatty acid fermentation products of the gut microbiome: implications in autism spectrum disorders. Microbial Ecology in Health & Disease 23, 19260.
Malkova, et al. (2012). Maternal immune activation yields offspring displaying mouse versions of the three core symptoms of autism. Brain Behav Immun 26, 607-616.
Mandel, et al. (2011), Maternal immune stimulation during pregnancy affects adaptive immunity in offspring to promote development of TH17 cells. Brain Behav Immun 25, 863-871.
Matsumoto, et al. (2012). Impact of Intestinal microbiota on intestinal luminal metabolome. Sci Rep 2, 233.
Mayer, E.A. (2011). Gut feelings: the emerging biology of gut-brain communication. Nat Rev Neurosci 12, 453-466.
Mazmanian, et al. (2008). A microbial symbiosis factor prevents intestinal inflammatory disease. Nature 453, 620-625.
Mazurek, et al. (2013). Anxiety, sensory over-responsivity, and gastrointestinal problems in children with autism spectrum disorders. J Abnorm Child Psychol 41, 165-176.
Ming, et al. (2012). Metabolic perturbance in autism spectrum disorders: a metabolomics study, Journal of proteome research 11, 5856-5862.
Mulder, et al. (2004). Platelet serotonin levels in pervasive developmental disorders and mental retardation: diagnostic group differences, within-group distribution, and behavioral correlates. J Am Acad Child Adolesc Psychiatry 43, 491-499.
Nicholson, et al. (2012). Host-gut microbiota metabolic interactions. Science 336, 1262-1267.
Nikolov, et al. (2009). Gastrointestinal symptoms in a sample of children with pervasive developmental disorders. J Autism Dev Disord 39, 405-413.
Novarino, et al, (2012). Mutations in BCKD-kinase lead to a potentially treatable form of autism with epilepsy. Science 338, 394-397.
Ochoa-Reparaz, et al. (2010). Central nervous system demyelinating disease protection by the human commensal Bacteroides fragilis depends on polysaccharide A expression. J Immunol 185, 4101-4108.

(56) References Cited

OTHER PUBLICATIONS

Odamaki, et al. (2008). Distribution of different species of the *Bacteroides fragilis* group in individuals with Japanese cedar pollinosis. Appl Environ Microbiol 74, 6814-6817.
Office Action dated Apr. 1, 2015 for European Patent Application No. 11831 629.8-1456 filed on Oct. 6, 2011.
Office Action dated Aug. 18, 2015 for Japanese Patent Application No. 2013-632955 filed Oct. 6, 2011 (with English translation).
Office Action dated Nov. 10, 2014 for European Patent Application No, 11831629.8 filed Oct. 6, 2011.
Office Action dated Nov. 21, 2013 for U.S. Appl. No. 13/267,748, filed Oct. 6, 2011.
O'Mahony, et al. (2009). Early life stress alters behavior, immunity, and microbiota in rats: implications for irritable bowel syndrome and psychiatric illnesses. Biological psychiatry 65, 263-267.
Onore, et al. (2012). The role of immune dysfunction in the pathophyslology of autism. Brain Behav Immun 26, 383-392.
Parracho, et al. (2005b). Differences between the gut microflora of children with autistic spectrum disorders and that of healthy children. Journal of medical microbiology 64, 987-991.
Patterson, Maternal Infection and Immune Involvement in Autism, Trends Mol Med 17, 389 (Jul. 2011).
Patterson, P. H. 2011. Modeling features of autism in animals. Pediatric Res 69:34R-40R.
Penagarikano et al., "Absence of CNTNAP2 Leads to Epilepsy, Neuronal Migration Abnormalities, and Core Autism-Related Deficits," Sep. 30, 2011, Cell, vol. 147, p. 235-246.
Perry, et al. (2007). Sensorimotor gating deficits in adults with autism, Biological psychiatry 61, 482-486.
Perslco, A.M., and Napolioni, V. (2013). Urinary p-cresol in autism spectrum disorder. Neurotoxicology and teratology 36, 82-90.
Portfors, C.V. (2007). Types and functions of ultrasonic vocalizations in laboratory rats and mice. J Am Assoc Lab Anim Sci 46, 28-34.
Price, et al. (2009). FastTree: Computing Large Minimum Evolution Trees with Profiles instead of a Distance Matrix. Mol Biol Evol 26, 1641-1650.
Pruesse, et al. (2012). SINA: Accurate high-throughput multiple sequence alignment of ribosomal RNA genes. BioInformatics 28, 1823-1829.
Quast, et al. (2013). The SILVA ribosomal RNA gene database project: improved data processing and web-based tools, Nucleic Acids Res 41, D590-D596.
Rao, et al. (2009). A randomized, double-blind, placebo-controlled pilot study of a probiotic in emotional symptoms of chronic fatigue syndrome. Gut Pathog 1, 6.
Resta-Lenert, S.C., and Barrett, K.E. (2009). Modulation of intestinal barrier properties by probiotics: role in reversing colitis. Ann N Y Acad Sci 1165, 175-182.
Riehle, et al. (2012). The Genboree Microbiome Toolset and the analysis of 16S rRNA microbial sequences. Bmc Bioinformatics 13.
Rong et al., "Cystathionine Beta Synthase Participates in Murine Oocyte Maturation Mediated by Homocysteine," Reprod. Toxicol., 24(1):89-96 (2007).
Rossignol, D.A., and Frye, R.E. (2012). Mitochondrial dysfunction in autism spectrum disorders: a systematic review and meta-analysis. Mol Psychiatry 17, 290-314.
Round et al.: "Coordination of tolerogenic immune responses by the commensal microbiota." J. Autoimmun., 34:J220-225 (2010).
Round, J.L., and Mazmanian, S.K, (2009). The gut microbiota shapes intestinal immune responses during health and disease. Nat Rev Immunol 9, 313-323.
Round, J.L., and Mazmanian, S.K. (2010). Inducible Foxp3+ regulatory T-cell development by a commensal bacterium of the Intestinal microbiota, Proc Natl Acad Sci U S A 107, 12204-12209.
Saldanha, A.J. (2004). Java Treeview-extensible visualization of microarray data. Bioinformatics 20, 3246-3248.
Sandler, et al. (2000). Short-term benefit from oral vancomycin treatment of regressive-onset autism. J Child Neural 15, 429-435.
Sankoorikal, et al. (2006). A mouse model system for genetic analysis of sociability: C57BL/6J versus BALB/cJ inbred mouse strains. Biological psychiatry 59, 415-423.
Scattoni, et al, (2011). Unusual repertoire of vocalizations in adult BTBR T+tf/J mice during three types of social encounters, Genes, brain, and behavior 10, 44-56.
Schmeisser, et al. (2012). Autistic-like behaviours and hyperactivity in mice lacking ProSAP1/Shank2. Nature 486, 256-260.
Schwartzer, et al. (2013). Maternal Immune activation and strain specific interactions in the development of autism-like behaviors in mice. Translational psychiatry 3, e240.
Segata, et al. (2011), Metagenomic biomarker discovery and explanation. Genome biology 12, R60.
Sharma, et al. (2010). Molecular modulation of Intestinal epithelial barrier: contribution of microbiota. Journal of biomedicine & biotechnology 2010, 305879.
Shi, et al. (2009). Activation of the maternal immune system alters cerebellar development in the offspring. Brain Behav Immun 23, 118-123.
Silverman, et al. (2010), Behavioural phenotyping assays for mouse models of autism, Nature Reviews Neuroscience 11, 490-502.
Smith et al., Host Genetics and Environmental Factors Regulate Ecological Succession of the Mouse Colon Tissue-Associated Microbiota, PLoS One 7 e30273 (Jan. 2012).
Smith, E.A., and Macfarlane, G.T. (1997). Formation of Phenolic and Indolic Compounds by Anaerobic Bacteria in the Human Large Intestine. Microb Ecol 33, 180-188.
Smith, et al. (2007). Maternal immune activation alters fetal brain development through interleukin-6. J Neurosci 27, 10695-10702.
Sommese, et al. (2012). Evidence of Bacteroides fragilis protection from Bartonella henselae-induced damage. PLoS One 7, e49653.
Song, et al. (2004). Real-time PCR quantitation of clostridia in feces of autistic children. Appl Environ Microblol 70, 6459-6465.
Suzuki, et al. (2011). Interleukin-6 (IL-6) regulates claudin-2 expression and tight junction permeability in intestinal epithelium. J Biol Chem 286, 31263-31271.
Tabuchi, et al. (2007). A neuroligin-3 mutation implicated in autism increases inhibitory synaptic transmission in mice. Science 318, 71-76.
Tamura, et al. (2011). Loss of claudin-15, but not claudin-2, causes Na+ deficiency and glucose malabsorption in mouse small intestine. Gastroenterology 140, 913-923.
Thomas, et al. (2009). Marble burying reflects a repetitive and perseverative behavior more than novelty-induced anxiety, Psychopharmacology 204, 361-373.
Tillisch, et al. (2013). Consumption of fermented milk product with problotic modulates brain activity. Gastroenterology 144, 1394-1401 e1394.
Tsai, et al, (2012), Autistic-like behaviour and cerebellar dysfunction in Purkinje cell Tsc1 mutant mice. Nature 488, 647-851.
Turner, J.R. (2009). Intestinal mucosal barrier function in health and disease. Nat Rev Immunol 9, 799-809.
Wang et al., "Is Urinary Indolyl-3-Aayloylglycine a Biomarker for Autism with Gastrointestinal Symptoms?," Biomarkers, 14(8):596-603 (2009).
Wang, et al. (2011), The prevalence of gastrointestinal problems in children across the United States with autism spectrum disorders from families with multiple affected members. Journal of developmental and behavioral pediatrics : JDBP 32, 351-360.
Wang, et al. (2012). Elevated fecal short chain fatty acid and ammonia concentrations in children with autism spectrum disorder. Dig Dis Sol 57, 2096-2102.
White, et al. (2009). Statistical Methods for Detecting Differentially Abundant Features in Clinical Metagenomic Samples. Plos Comput Biol 5.
White, J.F. (2003). Intestinal pathophyslology in autism. Exp Bid Med (Maywood) 228, 639-649.
Wikoff, et al. (2009), Metabolomics analysis reveals large effects of gut microflora on mammalian blood metabolites. Proc Natl Acad Sci U S A 106, 3698-3703.
Williams, et al. (2011). Impaired carbohydrate digestion and transport and mucosal dysbiosis in the intestines of children with autism and gastrointestinal disturbances. PLoS One 6, e24585.

(56) References Cited

OTHER PUBLICATIONS

Williams, et al. (2012), Application of novel PCR-based methods for detection, quantitation, and phylogenetic characterization of *Sutterella* species in intestinal biopsy samples from children with autism and gastrointestinal disturbances. MBio 3.
Wirtz, et al. (2007), Chemically induced mouse models of intestinal inflammation. Nature protocols 2, 541-546.
Wittebolle, et al. (2009), Initial community evenness favours functionality under selective stress. Nature 458, 623-626.
Won, et al. (2012). Autistic-like social behaviour in Shank2-mutant mice improved by restoring NMDA receptor function. Nature 486, 261-265.
Yang, et al. (2011). Automated three-chambered social approach task for mice. Curr Protoc Neurosci Chapter 8, Unit 8 26.
Yap, et al. (2010), Urinary metabolic phenotyping differentiates children with autism from their unaffected siblings and age-matched controls. Journal of proteome research 9, 2996-3004.
Office Action dated Oct. 5, 2016 in U.S. Appl. No. 14/839,041, filed Aug. 28, 2015.
Yadav, et al., "Pharmacological inhibition of gut-derived serotonin synthesis is a potential bone anabolic treatment for osteoporosis", Nature Medicine 16(3):308-312, 2010.
Nemeroff et al., "Are platelets the link between depression and ischemic heart disease?", American Heat Journal 140(4): S57-S62, 2000.
Office Action dated Jan. 25, 2017 issued in U.S. Appl. No. 14/925,510.
Office Action dated Mar. 29, 2017 issued in U.S. Appl. No. 14/012,769.
International Preliminary Report on Patentability dated May 2, 2017 issued in PCT/US2015/057897.
International Preliminary Report on Patentability dated May 2, 2017 issued in PCT/US2015/057888.
International Preliminary Report on Patentability dated May 2, 2017 issued in PCT/US2015/057891.
Office Action dated May 5, 2017 issued in U.S. Appl. No. 14/925,240.
Office Action dated Jun. 13, 2017 in Japanese Application No. 2015-530008.
Winek et al., "The Gut Microbiome as Therapeutic Target I Central Nervous System Diseases: Implications for Stroke", Neurotherapeutics 13(4): 762-774, 2016.
Gupta, "The phylogeny of proteobacteria: relationships to other eubacterial phyla and eukaryotes.", FEMS Microbiology Reviews 24 (4):367-402, 2000.
Jandhyala et al., "Role of the normal gut microbiota", World Journal of Gastroenterology 21(9): 8787-8803, 2015.
Lopetuso et al., "Commensal Clostridia: leading players in the maintenance of gut homeostasis", Gut Pathogens 5(1): 23, 2013.
Office Action dated May 25, 2017 in U.S. Appl. No. 14/839,041.
Office Action dated Aug. 12, 2016 for U.S. Appl. No. 14/925,510, filed Oct. 28, 2015.
Robinson, et al. "From Structure to Function: the Ecology of Host-Associated Microbial Communities" Microbiology and Molecular Biology Reviews, Sep. 2010, pp. 456-476.
American Psychiatric Association: Diagnostic and Statistical Manual of Mental Disorders, Fourth Edition, Text Revision. Washington, DC, pp. 69-84, American Psychiatric Association, 2000.
Seltzer, et al., "The Symptoms of Autism Spectrum Disorders in Adolescence and Adulthood" Journal of Autism and Developmental Disorders, vol. 33, No. 6, pp. 565-581, Dec. 2003.
Maslowski, et al., "Diet, gut microbiota and immune responses" Nature Immunology vol. 12 No. 1, pp. 5-9, Jan. 2011.
Office Action dated Feb. 7, 2017 for Japanese Patent Application No. 2016-088694 filed Apr. 27, 2016.
Petra, Louis, *"Does the human gut mircrobiota contribute to the etiology of autism spectrum disorders?"*; Digestive diseases and sciences, vol. 57, No. 8, Jun. 27, 2012, pp. 1987-1989.
Extended European Search Report dated Jun. 24, 2016, issued in EP Patent Application No. 16164727.6.
Notice of Allowance dated Jul. 6, 2016 in U.S. Appl. No. 13/267,748.
Partial Supplementary European Search Report dated May 2, 2016 issued in EP Patent Application No. 13832132.8.
Barbara, et al. (2005) "Interactions between commensal bacteria and gut sensorimotor function in health and disease" The American journal of gastroenterology 100, 2560-2568.
Extended European Search Report dated Jun. 24, 2016, issued in EP16164727.6.
Mandal, et al. (2011). Maternal immune stimulation during pregnancy affects adaptive immunity in offspring to promote development of TH17 cells. Brain Behav Immun 25, 863-871.
Nieswandt, et al. (2004) "Flow-cytometric analysis of mouse platelet function" Methods Mol Biol 272, 255-268.
Notice of Allowance dated Jul. 6, 2016 in U.S. Appl. No. 13/267,748, filed Oct. 6, 2011.
Office Action dated Nov. 18, 2015 in U.S. Appl. No. 13/267,748, filed Oct. 6, 2011.
Partial Supplementary European Search Report dated May 2, 2016 issued in EP 13832132.8.
Wang et al., "Is Urinary Indolyl-3-Acryloylglycine A Biomarker for Autism with Gastrointestinal Symptoms?" Biomarkers, 14(8):596-603 (2009).
Collins et al., The Interplay Between the Intestinal Microbiota and the Brain. Nature Reviews—Microbiology. 2012, 10(11):735-742.
Hsaio, Gastrointestinal Issues in Autism Spectrum Disorder. Harvard Review of Psychiatry. Mar.-Apr. 2014 vol. 22(2):104-111.
Hsaio et al., Microbiota Modulate Behavioral and Physiological Abnormalities Associated with Neurodevelopmental Disorders. Cell. 2013. vol. 155(7), p. 1451-1463.
International Search Report and Written Opinion dated Jun. 30, 2016 for international application PCT/US 15/57891.
Extended European Search Report dated Aug. 25, 2016, issued in EP13832132.8.
Office Action dated Aug. 22, 2017 in U.S. Appl. No. 14/925,510.
McTighe et al. (2013), The BTBR mouse model of autism spectrum disorders has learning and attentional impairments and alterations in acetylcholine nad kynurenic acid in prefrontal cortext. PLoS One 8; e62189, 11 pages.
Meyza et al. (2013), The BRBR T+tf/J mouse model for autism spectrum disorders-in search of biomarkers. Behavioural Brain Research 251: 25-34.
FAI Pre-Interview Communication dated Jun. 11, 2018 in the U.S. Appl. No. 15/893,456, filed Aug. 29, 2016.
Chen et al., "Exposure to the Functional Bacterial Amyloid Protein Curli Enhances Alpha-Synuciein Aggregation in Aged Fischer 344 Rats and Caenorhabditis elegans", Scientific Reports, vol. 6, pp. 1-10, 2016.
Farlow et al., "Parkinson Disease Overview", PubMed NCBI, https://www.ncbi.nlm.nih.gov/pubmed/20301402, GeneReviews, abstract pp. 1-2, printed May 14, 2018.
Hung et al.. "The Bacterial Amyloid Curli Is Associated with Urinary Source Bloodstream Infection", PLOS ONE, vol. 9, No. 1, pp. 1-6, Jan. 2014.
Lavatelli et al., "Proteomic typing of amyloid deposits in systematic amyloidoses", Amyloid, vol. 18, No. 4, pp. 177-182, 2011.
Office Action dated May 8, 2018 in Japanese Application No. 2015-530008 with English Translation.
International Search Report and Written Opinion dated May 14, 2018 in Application No. PCT/US2018/017116.
Borghi et al., Rett Syndrome: A Focus on Gut Microbiota, International Journal of Molecular Sciences, vol. 18, No. 2, pp. 1-17, Feb. 7, 2017.
De Theije, C., "Neuroimmunomodulation of the young brain: Nutrition, a Gut Feeling", The Netherlands: Utrecht University, pp. 1-78.
Strati et al., "Altered gut microbiota in Rett syndrome", Microbiome, vol. 4, No. 41, pp. 1-15, Jul. 30, 2016.
Yasui et al., "115q11.2-13.3 chromatin analysis reveals epigenetic regulation of CHRNA7 with deficiencies in Rett and autism brain", Human Molecular Genetics, vol. 20, No. 22, pp. 4311-4323, Aug. 12, 2011.
Office Action dated Jun. 21, 2018 in U.S. Appl. No, 14/012,769.
Office Action dated Jun. 12, 2018 in Australian Application No. 2013308826.

(56) References Cited

OTHER PUBLICATIONS

Office Action dated Jul. 4, 2018 in Canadian Application No. 2,881,656.
Office Action dated Jun. 22, 2018 in Chinese Application No. 201380056909.2 with English Translation.
Extended European Search Report dated Apr. 18, 2018 in Application No. 15855495.6.
Extended European Search Report dated May 2, 2018 in Application No. 15855218.2.
Extended European Search Report dated May 14, 2018 in Application No. 15856096.1.
Office Action dated Aug. 10, 2018 in U.S. Appl. No. 14/925,240.
International Search Report and Written Opinion dated Jul. 19, 2018 in Application No. PCT/US2018/018069.
RIA Science, "Scientists: Bacteria in the human body are not 10 times larger than their cells", accessible on the world wide web at https://ria.ru/science/20160111/1357907466.html, (with English Translation), updated Jan. 11, 2016, 14 pages. While this item bears an "updated" date of Jan. 11, 2016 as it refers to a web page, it may have been available in some form at an earlier point in time.
Office Action dated Aug. 22, 2018 in Eurasian Application No. 201790811 with English Translation.
Sender et al.. Revised Estimates for the Number of Human and Bacteria Cells in the Body. PLOS Biology. Aug. 19, 2016. 14(8) e1002533, in 10 pages.
Stephen et al. The Microbial Contribution to Human Faecal Mass. Journal of Medical Microbiology. 1980. 13: pp. 45-56.
MacFarlane et al., Chemotaxonomic Analysis of Bacterial Populations Colonizing the Rectal Mucosa in Patients with Ulcerative Colitis. Clinical Infectious Diseases. 2004. vol. 38, pp. 1690-1699.
Guarner et al. 2003. Gut flora in health and disease. The Lancet, vol. 361, Issue 9356, Feb. 8, 2003, pp. 512-519. PMID 12583961. Accessed Sep. 15, 2007.
Sears, C., A dynamic partnership: Celebrating our gut flora. Anaerobe. vol. 11, Issue 5, Oct. 2005, pp. 247-251.
Steinhoff, U., Who controls the crowd? New findings and old questions about the intestinal microflora. Immunology Letters. vol. 99, Issue 1, Jun. 15, 2005, pp. 12-16.
Gibson RG. 2004. Fibre and effects on probiotics (the preblotic concept). Clinical Nutrition Supplements, vol. 1, Issue 2, pp. 25-31.
Beaugerie et al. 2004. Antibiotic-associated diarrhoea. Best Practice & Research Clinical Gastroenterology, vol. 18, Issue 2, pp. 337-352.
Todar, K. The Normal Bacterial Flora of Humans. Accessible on the world wide web at www.textbookofbacteriology.normalflora.html. Todar's Online Textbook of Bacteriology (2012). As this item refers to a web page, it may have been available in some form at an earlier point in time.
Office Action dated Jan. 11, 2018 in European Application No. 13832132.8, filed Feb. 17, 2015.
Final Office Action dated Jan. 24, 2018 in U.S. Appl. No. 14/925,240.
Final Office Action dated Jan. 26, 2018 in U.S. Appl. No. 14/925,510.
Office Action dated Jul. 20, 2017 in Canadian Application No. 2,813,606, filed Oct. 6, 2011.
International Search Report dated Jan. 30, 2018 issued in PCT/US17/63108 filed Nov. 22, 2017.
Ono et al., "Antioxidant compounds have potent anti-fibrillogenic and fibril0destabilizing effects for α-synuclein fibrils in vitro", Journal of Neurochemistry, 2006, 97, 105-115.
Office Action dated Dec. 11, 2017 in U.S. Appl. No. 14/012,769.
Advisory Action dated Apr. 20, 2018 in U.S. Appl. No. 14/012,769.
Office Action dated Apr. 24, 2018 in the U.S. Appl. No. 15/249,870, filed Aug. 29, 2016.

\* cited by examiner

COMPOSITIONS AND METHODS COMPRISING BACTERIA FOR IMPROVING BEHAVIOR IN NEURODEVELOPMENTAL DISORDERS

CROSS-REFERENCE TO RELATED APPLICATIONS

The present application claims the benefit of U.S. Provisional Application No. 62/072,873, filed on Oct. 30, 2014, which is hereby incorporated by reference in its entirety.

STATEMENT REGARDING FEDERALLY SPONSORED R&D

This invention was made with government support under Grant No. W81XWH-11-1-0515 awarded by the Army Research Office. The government has certain rights in the invention.

BACKGROUND

Field

Some embodiments described herein relate generally to probiotic compositions, which can be used to treat autism spectrum disorder (ASD) symptoms.

Background

Autism spectrum disorder (ASD) is a class of neurodevelopmental diseases characterized by the presence and severity of repetitive behaviors and deficits in social interaction and communication. The prevalence of ASD has continued to rise, with a current 1 in 68 children in the United States diagnosed with ASD (CDC, 2012), and similar prevalences in other countries worldwide. ASD is believed to be caused by a combination of genetic and environmental risk factors. Numerous pre-clinical studies demonstrate that modeling maternal immune activation (MIA) in rodents and monkeys sufficiently causes the development of ASD-related neuropathological and behavioral abnormalities in the offspring.

SUMMARY

In accordance with some embodiments described herein, methods for improving a communication behavior or sensorimotor gating performance in a subject in need of such improvement are provided. In some embodiments, the method comprises identifying a subject having autism spectrum disorder symptoms or schizophrenia symptoms in need of improving communication behavior or sensorimotor gating performance. In some embodiments, the method comprises administering to the subject an effective amount of one or more *Enterococcus* bacteria. In some embodiments, the subject suffers from anxiety, autism spectrum disorder (ASD), schizophrenia, or a gastrointestinal or immunological pathology associated with one or more of the symptoms of ASD. In some embodiments, the subject is in need of improving sensorimotor gating. In some embodiments, the subject is in need of improving sensorimotor gating and a communication behavior. In some embodiments, the communication behavior in need of improvement comprises at least one of impaired sociability, impaired language comprehension, impaired language production, or impaired communication. In some embodiments, a sole active ingredient administered to the subject in the method consists essentially of the one or more *Enterococcus* bacteria. In some embodiments, the effective amount of the one or more *Enterococcus* bacteria is in a composition substantially free of bacteria other than the *Enterococcus* bacteria. In some embodiments, the one or more *Enterococcus* bacteria comprises *E. faecalis*. In some embodiments, a sole active ingredient administered to the subject in the method consists essentially of *E. faecalis*. In some embodiments, the effective amount of the one or more *Enterococcus* bacteria is in a composition substantially free of bacteria other than the *E. faecalis*. In some embodiments, the method further comprises administering an effective amount of one or more *Bacteroides* bacteria to the subject. In some embodiments, the one or more *Bacteroides* bacteria comprises *B. thetaiotaomicron*, *B. vulgatus*, or a mixture of these bacteria. In some embodiments, the one or more *Bacteroides* bacteria comprises *B. fragilis*, *B. thetaiotaomicron*, *B. vulgatus*, or a mixture of these bacteria. In some embodiments, the one or more *Bacteroides* bacteria comprises *B. thetaiotaomicron*, *B. vulgatus*, or *B. fragilis* or a mixture of two or three of these two bacteria (e.g., *B. thetaiotaomicron* and *B. vulgatus*; *B. thetaiotaomicron* and *B. fragilis*, *B. vulgatus*, and *B. fragilis*, or *B. thetaiotaomicron*, *B. vulgatus*, and *B. fragilis*). In some embodiments, a sole active ingredient administered to the subject in the method consists essentially of a mixture of one or more *Enterococcus* bacteria and one or more *Bacteroides* bacteria. In some embodiments, effective amount of one or more *Enterococcus* bacteria and the effective amount of one or more *Bacteroides* bacteria are in a composition substantially free of bacteria other than the *Enterococcus* bacteria and *Bacteroides* bacteria. In some embodiments, a sole active ingredient administered to the subject in the method consists essentially of: a mixture of *Enterococcus* bacteria and *B. thetaiotaomicron*; a mixture of *Enterococcus* bacteria and *B. vulgatus*; or a mixture of *Enterococcus* bacteria, *B. thetaiotaomicron*, and *B. vulgatus*. In some embodiments, a sole active ingredient administered to the subject in the method consists essentially of a mixture of *Enterococcus* bacteria and *B. fragilis*; a mixture of *Enterococcus* bacteria and *B. thetaiotaomicron*; a mixture of *Enterococcus* bacteria and *B. vulgatus*; a mixture of *Enterococcus* bacteria, *B. fragilis*, and *B. thetaiotaomicron*; a mixture of *Enterococcus* bacteria, *B. fragilis*, and *B. vulgatus*; a mixture of *Enterococcus* bacteria, *B. thetaiotaomicron*, and *B. vulgatus*; or a mixture of *Enterococcus* bacteria, *B. fragilis*, *B. thetaiotaomicron*, and *B. vulgatus*. In some embodiments, the effective amount of the one or more *Enterococcus* bacteria is administered separately from the effective amount of the one or more *Bacteroides* bacteria, and each of the effective amount of the one or more *Enterococcus* bacteria and the effective amount of the one or more *Bacteroides* bacteria are administered substantially free of bacteria other than the *Enterococcus* bacteria and *Bacteroides* bacteria. In some embodiments, the effective amount of the one or more *Enterococcus* bacteria and the effective amount of the one or more *Bacteroides* bacteria are in a composition substantially free of bacteria other than *Enterococcus* bacteria, *B. thetaiotaomicron*, and *B. vulgatus*. In some embodiments, the effective amount of the one or more *Enterococcus* bacteria and the effective amount of the one or more *Bacteroides* bacteria are in a composition substantially free of bacteria other than *Enterococcus* bacteria, *B/fragilis*, *B. thetaiotaomicron*, and *B. vulgatus*. In some embodiments, the effective amount of the one or more *Enterococcus* bacteria is effective when administered in combination with a *Bacteroides* bacteria. In some embodiments, the effective amount of one or more *Enterococcus* bacteria comprises at least about $10^7$ colony forming units (cfu), for example at least about $10^7$ cfu, at least about $10^8$ cfu, at least about $10^9$ cfu, at least about $10^{10}$ cfu, at least about $10^{11}$ cfu, or at least about $10^{12}$ cfu.

In some embodiments, a composition is provided. The composition can comprise an *Enterococcus* bacteria and a *Bacteroides* bacteria. In some embodiments, the composition is substantially free of bacteria other than *E. faecalis, B. thetaiotaomicron* and *B. vulgatus*. In some embodiments, the composition is substantially free of bacteria other than *E. faecalis, B. fragilis, B. thetaiotaomicron* and *B. vulgatus*. In some embodiments, the composition is comprises a mixture of *Enterococcus* bacteria and *B. thetaiotaomicron*; a mixture of *Enterococcus* bacteria and *B. vulgatus*; or a mixture of *Enterococcus* bacteria, *B. thetaiotaomicron*, and *B. vulgatus*. In some embodiments, the composition comprises a mixture of *Enterococcus* bacteria and *B. thetaiotaomicron*; a mixture of *Enterococcus* bacteria and *B. fragilis*; a mixture of *Enterococcus* bacteria and *B. vulgatus*; a mixture of *Enterococcus* bacteria, *B. thetaiotaomicron*, and *B. vulgatus*; a mixture of *Enterococcus* bacteria, *B. fragilis*, and *B. vulgatus*; a mixture of *Enterococcus* bacteria, *B. thetaiotaomicron*, and *B. fragilis*; or a mixture of *Enterococcus* bacteria, *B. fragilis*, *B. thetaiotaomicron*, and *B. vulgatus*. In some embodiments, the composition comprises at least about $10^7$ colony forming units (cfu) of *Enterococcus* bacteria, for example at least about $10^7$ cfu, at least about $10^8$ cfu, at least about $10^9$ cfu, at least about $10^{10}$ cfu, at least about $10^{11}$ cfu, or at least about $10^{12}$ cfu. In some embodiments, the composition comprises at least about $10^7$ colony forming units (cfu) of *Bacteroides* bacteria, for example at least about $10^7$ cfu, at least about $10^8$ cfu, at least about $10^9$ cfu, at least about $10^{10}$ cfu, at least about $10^{11}$ cfu, or at least about $10^{12}$ cfu.

BRIEF DESCRIPTION OF THE DRAWINGS

FIG. 2A depicts center entries. FIG. 2B depicts center duration(s).

FIG. 4A is a graph illustrating that treatment in accordance with some embodiments described herein significantly increases total number of calls produced. FIG. 4B is a graph illustrating that treatment in accordance with some embodiments described herein significantly increases average duration per call. FIG. 4C is a graph illustrating that treatment in accordance with some embodiments described herein significantly increases total call duration.

With reference to FIGS. 2A, 2B, 3, 4A, 4B, 4C, and 5, data are shown for Saline (10), Saline+*B. fragilis* (11), Poly(I:C) (12), Poly(I:C)+*B. fragilis* (13), Poly(I:C)+*B. fragilis* dPSA (14), Poly(I:C)+*B. thetaiotaomicron* (15), Poly (I:C)+*B. vulgatus* (16), and Poly (I:C)+*E. faecalis* (17).

DETAILED DESCRIPTION

Figure 1:
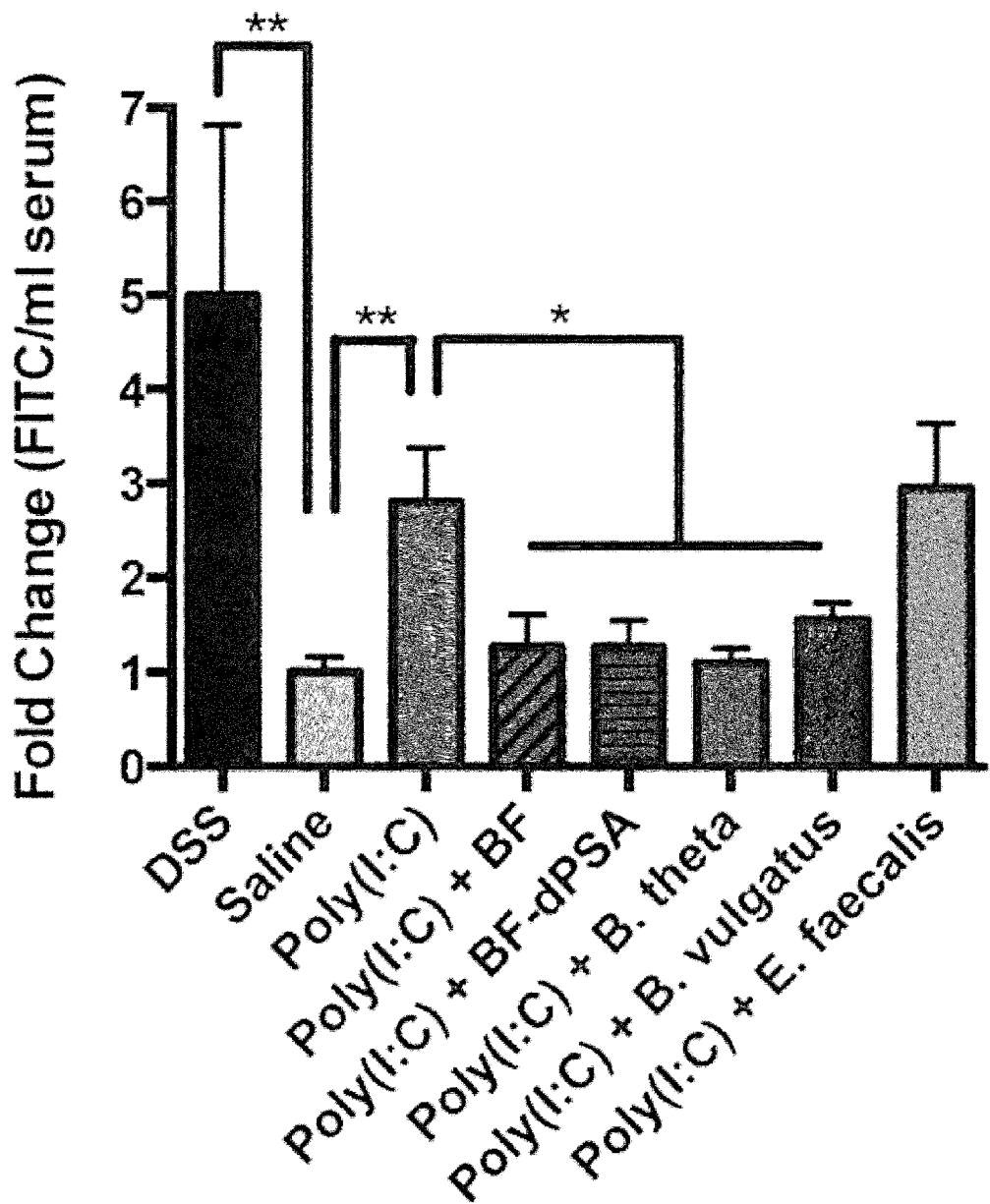
FIG. 1 is a graph illustrating that acute postnatal treatment with *B. fragilis*, mutant *B. fragilis* lacking polysaccharide A (dPSA), *B. thetaiotaomicron*, and *B. vulgatus*, but not *E. faecalis* corrects defects in intestinal barrier integrity in the maternal immune activation (MIA) mouse model for autism in accordance with some embodiments described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Without being limited by any theory, it is contemplated that there can be a gut-immune-brain connection in autism spectrum disorders (ASD). In accordance with some embodiments described herein, compositions comprising one or more bacterial species (for example, probiotic compositions) are provided, which can be administered to a subject to treat one or more symptoms of ASD, for example sensorimotor gating behavior deficiencies and/or communication behavior deficiencies. In some embodiments, one or more of the following bacteria is administered to a subject: *Bacteroides fragilis, Bacteroides thetaiotaomicron, Bacteroides vulgatus*, and *Enterococcus faecalis*, so as to improve sensorimotor gating behavior and/or communication behavior deficiencies in the subject.

Maternal infection is regarded as a primary environmental risk factor for ASD, as well as other neurodevelopmental disorders such as schizophrenia. Several large epidemiological studies indicate that maternal bacterial or viral infection during pregnancy increases the risk for ASD in the offspring. Similar findings link elevated levels of immune signaling factors, such as cytokines and chemokines, in the maternal serum or amniotic fluid during pregnancy to increased ASD risk.

In addition to its core diagnostic features, ASD is also associated with several co-morbid medical conditions. Immune dysregulation and gastrointestinal issues are of particular interest, in light of their high prevalences in ASD and their correlation with the severity of cardinal ASD-related behavioral impairments. A significant subset of individuals with ASD present with gastrointestinal distress, including constipation, abdominal pain, immune activation and intestinal barrier dysfunction ("leaky gut"). In addition, several studies report that the composition of gut bacteria (the intestinal microbiome) is altered in children with ASD compared to controls. Without being limited by any theory, it is contemplated herein that there is a potential gut-immune-brain connection in ASD.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

As used herein, the term "subject" is a vertebrate, such as a mammal. The term "mammal" is defined as an individual belonging to the class Mammalia and includes, without limitation, humans, domestic and farm animals, and zoo, sports, or pet animals, such as sheep, dogs, horses, cats or cows. In some embodiments, the subject is human. In some embodiments, the subject is a non-human primate.

As used herein, the term "condition/disorder/symptom" or "behavioral abnormality" refers to a symptom expressed by a subject including but not limited to anxiety, Fragile X, Rett syndrome, tuberous sclerosis, obsessive compulsive disorder, attention deficit disorder, schizophrenia, autistic disorder (classic autism), Asperger's disorder (Asperger syndrome), pervasive developmental disorder not otherwise specified (PDD-NOS), childhood disintegrative disorder (CDD), or a pathological condition with one or more of the symptoms of ASD.

As used herein, the term "subject in need of the treatment" refers to a subject expressing or suffering from one or more of the behavioral disorder/symptoms mentioned above. In some embodiments, the subject in need of treatment suffers from at least one of schizophrenia, ASD, or a gastrointestinal or immunological pathology associated with ASD or schizophrenia (for example leaky gut syndrome). An appropriately qualified person is able to identify such an individual in need of treatment using standard behavioral testing protocols/guidelines. The same behavioral testing protocols/guidelines can also be used to determine whether there is improvement to the individual's disorder and/or symptoms. As used herein "sensorimotor gating" refers to ability to filter out irrelevant and/or intrusive sensory stimuli. As such, subjects deficient in sensorimotor gating behavior can have impaired ability to filter out stimuli, and/or can have difficulty coping with intensely stimulating environments. By way of example, sensorimotor gating behavior can be assessed with a pre-pulse inhibition (PPI) test. In accordance with some embodiments described herein a subject is identified as being in need of improved sensorimotor gating, for example in need of improving filtering out of irrelevant sensory stimuli such as background noise, background light, and the like. As used herein, "communication behavior" refers to communication, language comprehension and production, and/or sociability, including vocal and non-vocal social communication. In some embodiments, a subject is identified as deficient in communication behavior based on impaired sociability. In some embodiments, a subject is identified as deficient in communication behavior based on impaired language comprehension and/or production.

As used herein, the term "improvement in behavioral performance" refers to prevention or reduction in the severity or frequency, to whatever extent, of one or more of the behavioral disorders, symptoms and/or abnormalities expressed by individual suffering from ASD, schizophrenia, or a pathological condition with one or more of the symptoms of ASD or schizophrenia. Non-limiting examples of the behavioral symptoms include impaired communication, impaired sociability, impaired language comprehension and/or production, impaired sensorimotor gating behavior, repetitive behavior, and increased anxiety. The improvement is either observed by the individual taking the treatment themselves or by another person (medical or otherwise). In some embodiments, a probiotic comprising an effective amount of *Bacteroides* and/or *Enterococcus* bacteria as described herein is administered the subject. In some embodiments, sensorimotor gating behavior is improved in the subject after administration of the probiotic. In some embodiments, communication behavior is improved in the subject after administration of the probiotic. Examples of communication behaviors that can be improved include communication, sociability, and language comprehension and/or production. In some embodiments, anxiety behavior is improved in the subject after administration of the probiotic. In some embodiments, repetitive behavior is improved in the subject after administration of the probiotic. In some embodiments, sensorimotor gating behavior and communication behavior are improved in the subject after administration of the probiotic.

As used herein, the term "treatment" refers to a clinical intervention made in response to a disease, disorder or physiological condition manifested by a subject, particularly a subject suffering from ASD, schizophrenia, or a pathological condition with one or more of the symptoms of ASD or schizophrenia. The aim of treatment may include, but is not limited to, one or more of the alleviation or prevention of symptoms, slowing or stopping the progression or worsening of a disease, disorder, or condition and the remission of the disease, disorder or condition. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may improve behavioral performance of the subject, including ASD-related behaviors such as sensorimotor gating behavior deficiencies and/or communication behavior deficiencies. As used herein, the term "prevention" refers to any activity that reduces the burden of the individual later expressing those behavioral symptoms. This takes place at primary, secondary and tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications.

"Pharmaceutically acceptable" carriers are ones which are nontoxic to the cell or mammal being exposed thereto at the dosages and concentrations employed. "Pharmaceutically acceptable" carriers in accordance with methods and uses and compositions and kits herein can comprise, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as TWEEN™ surfactant, polyethylene glycol (PEG), and PLURONICS™ surfactant. Auxiliary, stabilizer, emulsifier, lubricant, binder, pH adjustor controller, isotonic agent and other conventional additives may also be added to the carriers.

The pharmaceutically acceptable or appropriate carrier in accordance with methods and uses and compositions and kits herein may include other compounds known to be beneficial to an impaired situation of the GI tract (e.g., antioxidants, such as Vitamin C, Vitamin E, Selenium or Zinc); or a food composition. The food composition can be, but is not limited to, milk, yoghurt, curd, cheese, fermented milks, milk based fermented products, ice-creams, fermented cereal based products, milk based powders, infant formulae, tablets, liquid bacterial suspensions, dried oral supplement, or wet oral supplement.

As used herein, the term "probiotic" refers to live microorganisms, which, when administered in adequate amounts, confer a health benefit on the host. The probiotics in accordance with methods and uses and compositions and kits herein may be available in foods and dietary supplements (for example, but not limited to capsules, tablets, powders, and liquids). Non-limiting examples of foods containing probiotic include dairy products such as yogurt, fermented and unfermented milk, smoothies, butter, cream, hummus, kombucha, salad dressing, miso, tempeh, nutrition bars, and some juices and soy beverages. In some embodiments, the probiotic comprises a single microorganism. In some embodiments, the probiotic comprises a combination of microorganisms. In some embodiments, the probiotic comprises a single composition. In some embodiments, the probiotic comprises two or more compositions, which can be used together, for example administered simultaneously or administered sequentially. It is noted that a probiotic can serve as the "active ingredient" or a composition or compositions for use in administration to a subject. That is, the method, use, and/or composition or compositions (either individually or in the aggregate) can comprise an effective amount of probiotic to improve at least one behavior in a subject. In some embodiments, the probiotic is the sole active ingredient for administration to the subject. In some embodiments, the "sole active ingredient" probiotic for administration to the subject can be provided in a composition or in a method or use that is substantially free of or free of bacteria other than the probiotic, antibiotics, and drugs. Even if the probiotic is the "sole" active ingredient, the composition or composition comprising the probiotic may comprise additional substances (such as buffers, bacterial feedstock, excipients, flavors, and/or food) that do not substantially affect the behavior of the subject, but may be useful for the function of the probiotic or its administration.

In some embodiments, the probiotic is comprised in a composition or compositions that are substantially free of bacteria (other than the probiotic) and/or drugs or antibiotics. By "substantially free" or "substantially absent", it is understood that while a bacteria other than the probiotic, drug, and/or antibiotic may be present in trace amounts, the bacteria other than the probiotic, drug, and/or antibiotic have no appreciable effect on the subject.

As used herein "effective amount" of probiotic refers to a quantity sufficient to achieve a clinically significant change in a behavior of a subject.

As used herein, the term "neutraceutical" refers to a food stuff (as a fortified food or a dietary supplement) that provides health benefits. Nutraceutical foods are not subject to the same testing and regulations as pharmaceutical drugs.

Probiotics for Treatment of ASD and/or Schizophrenia Symptoms

Without being limited by any theory, it is contemplated that the MIA mouse model for autism, which displays both neuropathological and behavioral features of ASD and also schizophrenia, and also exhibits immunological and gastrointestinal abnormalities relevant to the human disorder. It is demonstrated herein that treatment of MIA offspring with human commensal bacteria such as *Bacteroides fragilis* corrects particular gastrointestinal and behavioral deficits. Accordingly, some embodiments include a probiotic treatment for symptoms of ASD and/or schizophrenia.

Figure 2A:
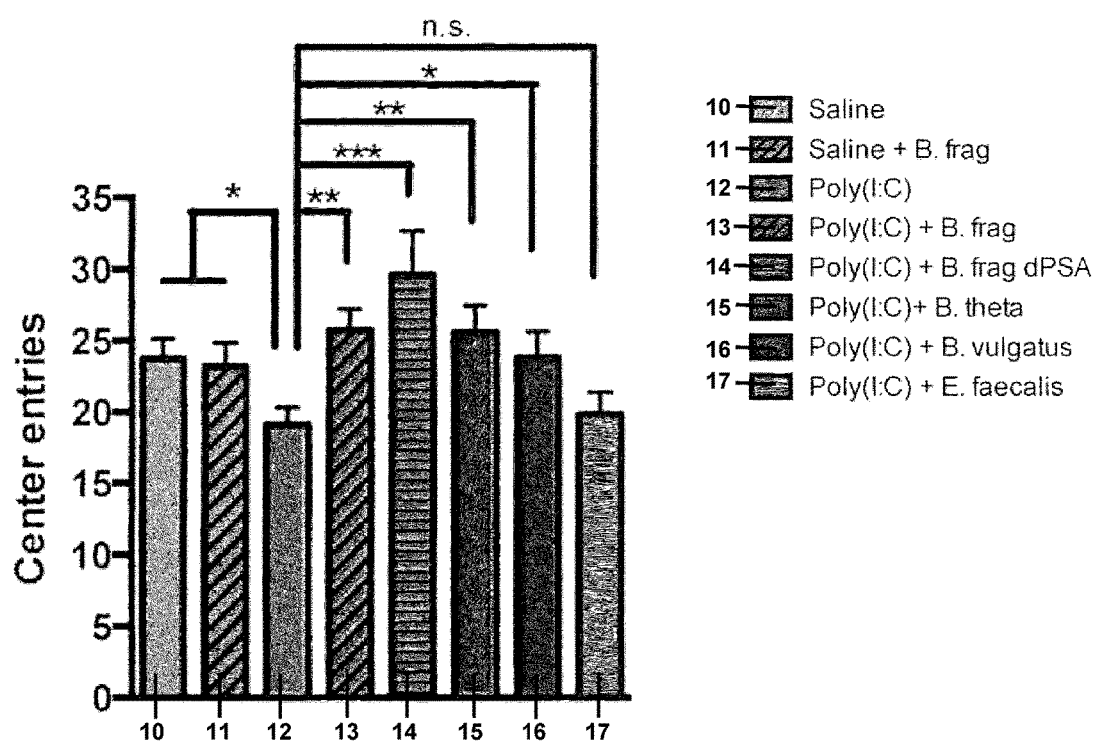
FIGS. 2A-2B are a series of graphs illustrating that acute postnatal treatment with *B. fragilis*, mutant *B. fragilis* lacking polysaccharide A (dPSA), *B. thetaiotaomicron*, and *B. vulgatus*, but not *E. faecalis* corrects anxiety-like behaviors in the maternal immune activation (MIA) mouse model for autism in accordance with some embodiments described herein.
Figure 2B:
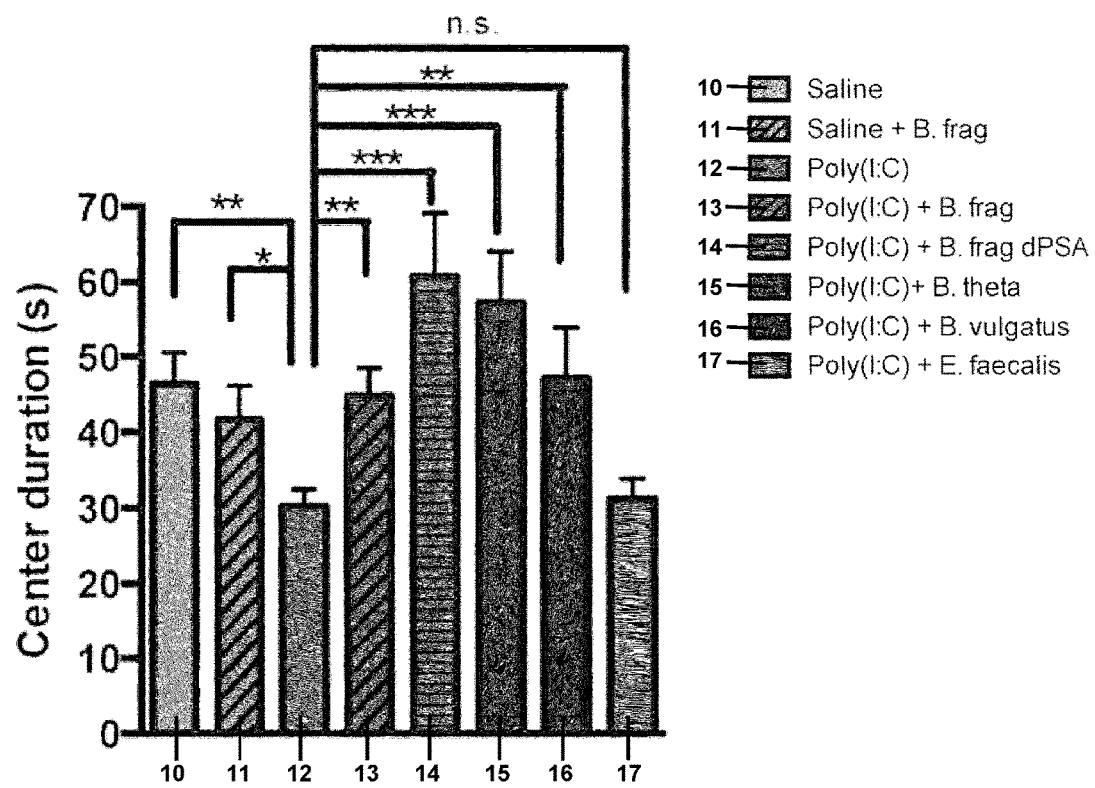
Figure 3:
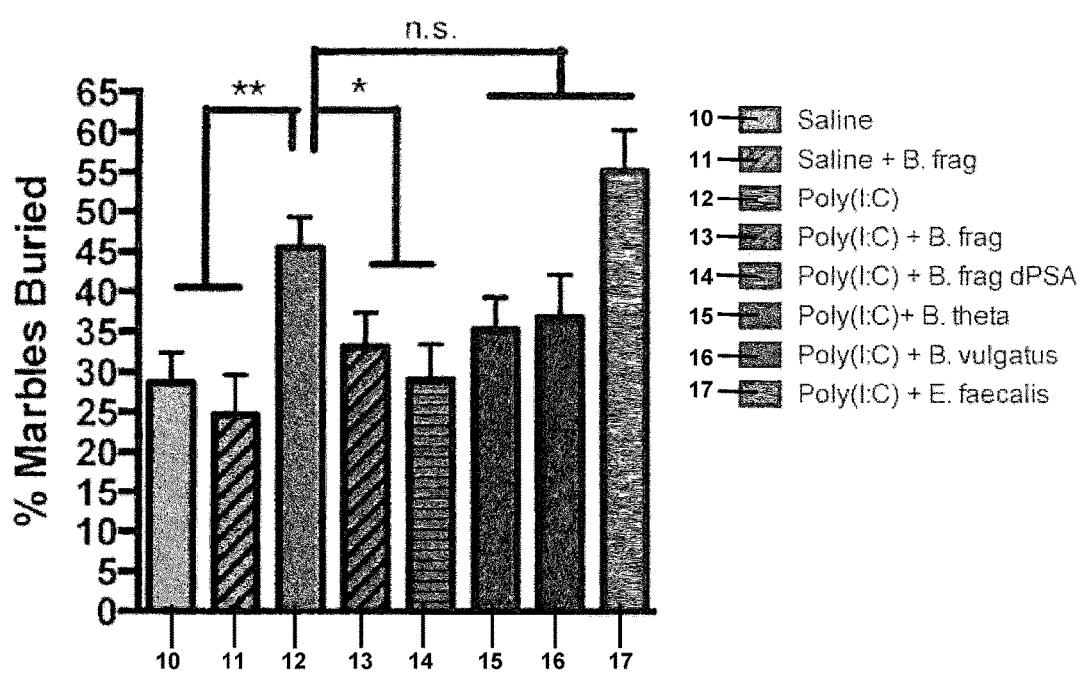
FIG. 3 is a graph illustrating that acute postnatal treatment with *B. fragilis*, mutant *B. fragilis* lacking polysaccharide A (dPSA), *B. thetaiotaomicron*, and *B. vulgatus*, but not *E. faecalis* improves repetitive behaviors in the maternal immune activation (MIA) mouse model for autism in accordance with some embodiments described herein.
Figure 4A:
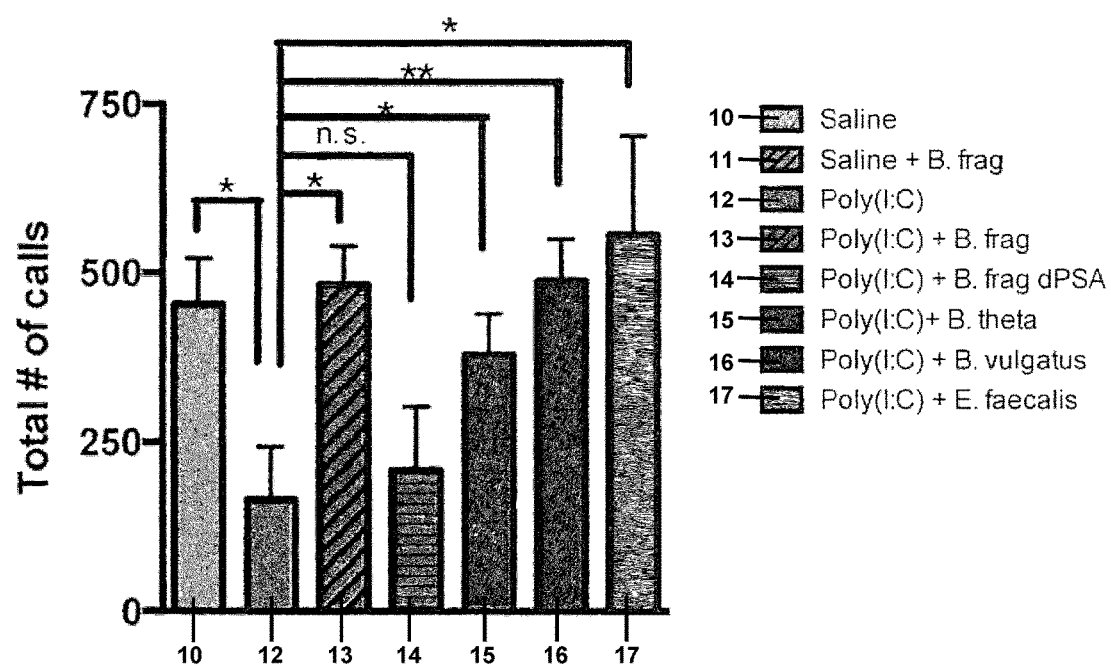
FIGS. 4A-4C are a series of graphs illustrating that that acute postnatal treatment with *B. fragilis*, *B. thetaiotaomicron*, *B. vulgatus*, and *E. faecalis* improves communication behavior in the maternal immune activation (MIA) mouse model for autism in accordance with some embodiments described herein.
Figure 4B:
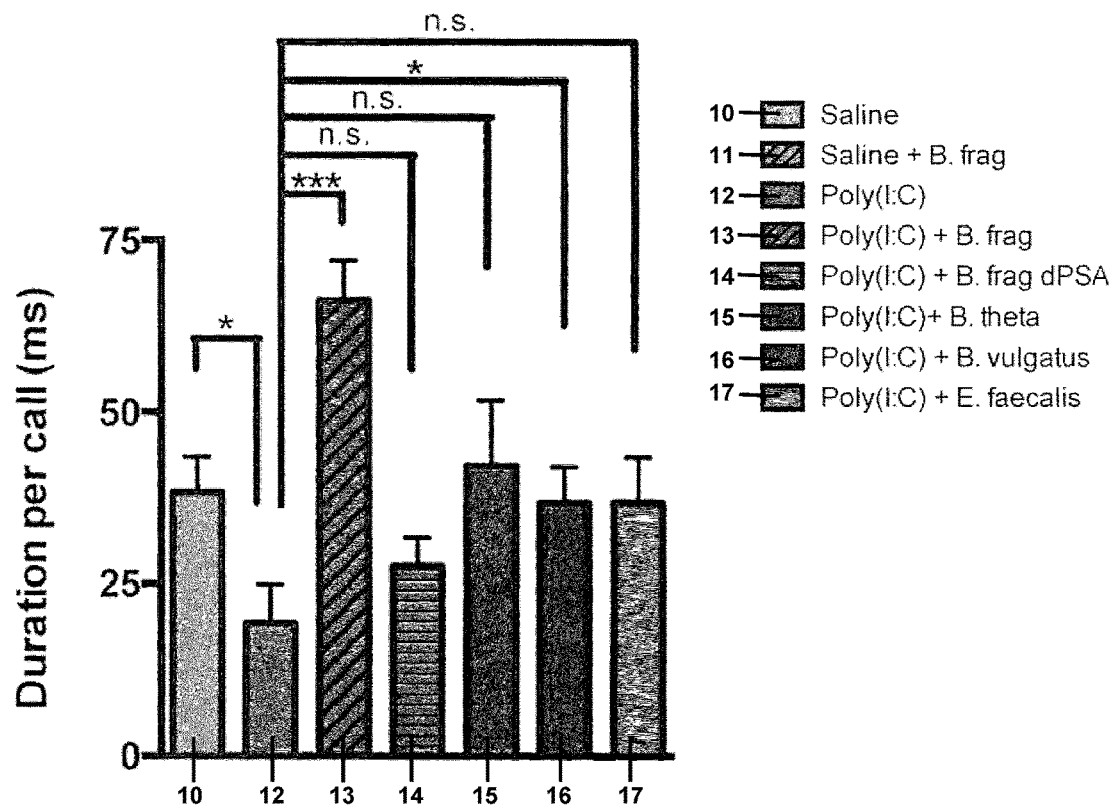
Figure 4C:
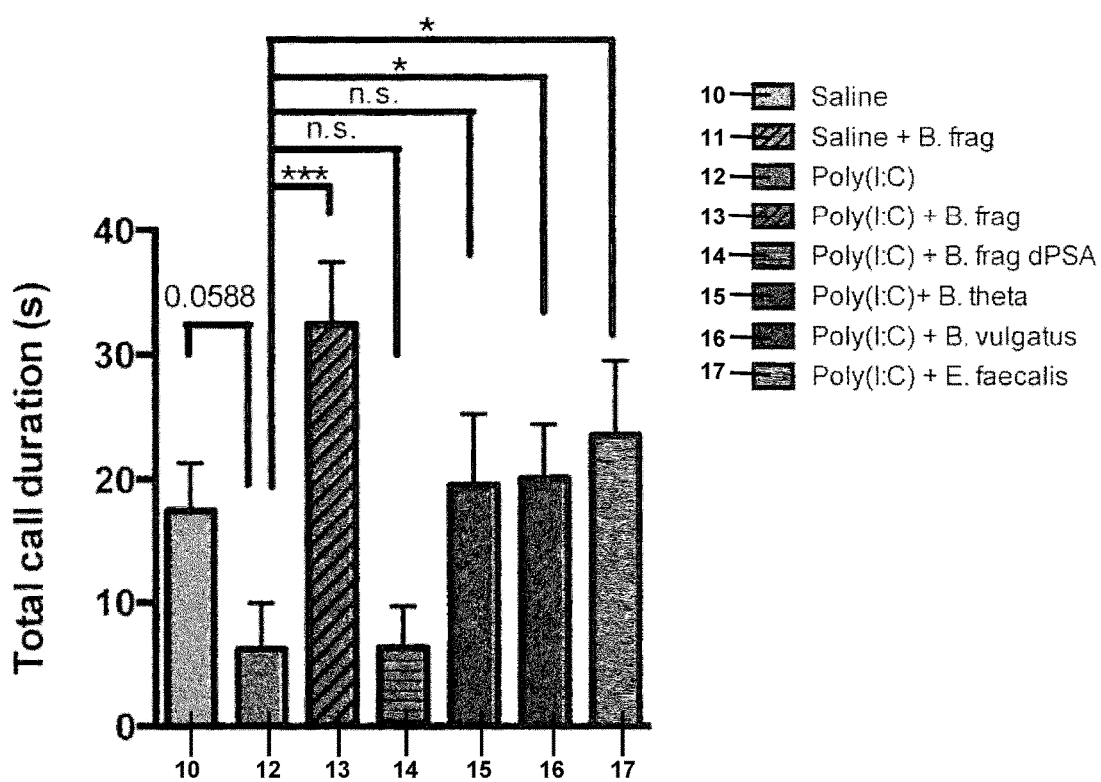
Figure 5:
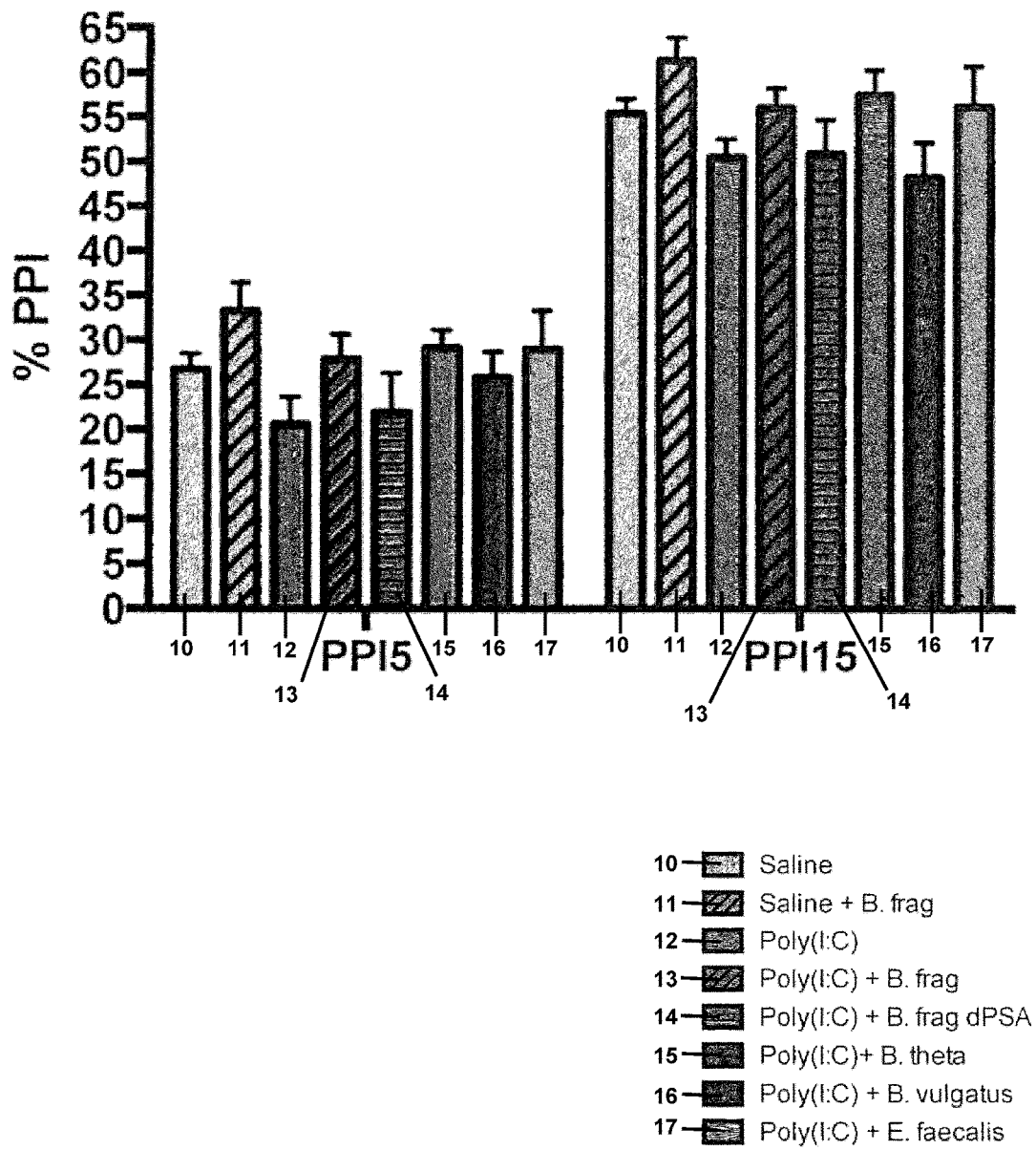
FIG. 5 is a graph illustrating that acute postnatal treatment with *B. fragilis, B. thetaiotaomicron*, and *E. faecalis* improves sensorimotor gating behavior in the maternal immune activation (MIA) mouse model for autism in accordance with some embodiments described herein.

*Bacteroides fragilis* has been observed to have immunomodulatory properties. Unexpectedly, it has been demonstrated herein that other bacterial species can confer a probiotic treatment in MIA mice. 3-week old MIA offspring were treated with *Bacteroides thetaiotaomicron, Bacteroides vulgatus*, or *Enterococcus faecalis* for one week, and then assayed for ASD-related gastrointestinal and behavioral symptoms. It is shown that that treatment with *B. thetaiotaomicron* or *B. vulgatus* corrects deficits in intestinal barrier integrity in MIA offspring, whereas treatment with *E. faecilis* has no significant effect (see FIG. 1). In addition, *B. thetaiotaomicron* and *B. vulgatus* treatment improve anxiety-like, repetitive and communication behavior in MIA mice (see FIGS. 2-4). *B. thetaiotaomicron* and *E. faecalis* improve sensorimotor gating behavior deficiencies in MIA mice (FIG. 5). Accordingly, in some embodiments described herein, probiotic treatments for ASD-related behaviors are provided. The treatment can comprise administering a probiotic comprising, consisting essentially of, or consisting of *B. fragilis, B. thetaiotaomicron, B. vulgatus*, or *E. faecilis*, or a combination of two, three, or four of these bacteria as described herein to a subject in need of behavioral performance. The subject can be in need of improvement in sensorimotor gating, and/or communication behavior.

In some embodiments, the subject is in need of improvement in sensorimotor gating behavior, and an effective amount of a probiotic comprising, consisting of, or consisting essentially of at least one of the following is provided for administration to the subject (or is for use in treating the subject): (a) *Enterococcus* bacteria (e.g., *E. faecilis E. faecium, E. hirae, E. avium, E. durans, E. gallinarum*, or *E. casseliflavus*); (b) *Enterococcus* bacteria (e.g., *E. faecilis, E. faecium, E. hirae, E. avium, E. durans, E. gallinarum*, or *E. casseliflavus*); and *Bacteroides* bacteria (e.g., *B. fragilis, B. thetaiotaomicron* or *B. vulgatus*); (c) *Enterococcus* bacteria and *B. fragilis*; (d) *Enterococcus* bacteria and *B. thetaiotaomicron*; (d) *Enterococcus* bacteria and *B. vulgatus*; (e) *Enterococcus* bacteria, *B. fragilis*, and *B. thetaiotaomicron*, (f) *Enterococcus* bacteria, *B. fragilis*, and *B. vulgatus*; (g) *Enterococcus* bacteria, *B. thetaiotaomicron* and *B. vulgatus*; (h) *Enterococcus* bacteria, *B. fragilis, B. thetaiotaomicron* and *B. vulgatus*; (i) *E. faecilis* and *B. fragilis*; (j) *E. faecilis* and *B. thetaiotaomicron*; (k) *E. faecilis* and *B. vulgatus*; (l) *E. faecilis, B. fragilis*, and *B. thetaiotaomicron*, (m) *E.* faecilis, B. fragilis, and B. vulgatus; (n) E. faecilis, B. thetaiotaomicron and B. vulgatus; (o) E. faecilis, B. fragilis, B. thetaiotaomicron and B. vulgatus; (p) Bacteroides bacteria; (q) B. fragilis and B. thetaiotaomicron; (r) B. fragilis, and B. vulgatus; (s) B. thetaiotaomicron and B. vulgatus; or (t) B. fragilis, B. thetaiotaomicron and B. vulgatus. Following administration of the bacteria, the sensorimotor gating behavior can be improved. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the *B. fragilis* comprises wild-type *B. fragilis*, mutant *B. fragilis* lacking polysaccharide A (dPSA), or a combination of wild-type *B. fragilis* and dPSA *B. fragilis*. In some embodiments, the sensorimotor gating behavior comprises or correlates with frequency of pre-pulse inhibition. In some embodiments, the subject has communication behavior deficiencies associated with ASD, for example deficient communication, sociability, and language comprehension and/or production. In some embodiments, the subject has sensorimotor gating behavior deficiencies associated with ASD. In some embodiments, the subject has communication behavior deficiencies associated with schizophrenia, for example deficient communication, sociability, and language comprehension and/or production. In some embodiments, the subject has sensorimotor gating behavior deficiencies associated with schizophrenia.

In some embodiments, the subject is in need of improvement in communication behavior, and an effective amount of a probiotic comprising, consisting of, or consisting essentially of at least one of the following is provided for administration to the subject (or is for use in treating the subject): (a) *Enterococcus* bacteria (e.g., *E. faecilis, E. faecium, E. hirae, E. avium, E. durans, E. gallinarum,* or *E. casseliflavus*); (b) *Enterococcus* bacteria (e.g., *E. faecilis, E. faecium, E. hirae, E. avium, E. durans, E. gallinarum,* or *E. casseliflavus*); and *Bacteroides* bacteria (e.g., *B. fragilis, B. thetaiotaomicron* or *B. vulgatus*); (c) *Enterococcus* bacteria and *B. fragilis*; (d) *Enterococcus* bacteria and *B. thetaiotaomicron*; (d) *Enterococcus* bacteria and *B. vulgatus*; (e) *Enterococcus* bacteria, *B. fragilis,* and *B. thetaiotaomicron,* (f) *Enterococcus* bacteria, *B. fragilis,* and *B. vulgatus*; (g) *Enterococcus* bacteria, *B. thetaiotaomicron* and *B. vulgatus*; (h) *Enterococcus* bacteria, *B. fragilis, B. thetaiotaomicron* and *B. vulgatus*; (i) *E. faecilis* and *B. fragilis*; (j) *E. faecilis* and *B. thetaiotaomicron*; (k) *E. faecilis* and *B. vulgatus*; (1) *E. faecilis, B. fragilis,* and *B. thetaiotaomicron,* (m) *E. faecilis, B. fragilis,* and *B. vulgatus*; (n) *E. faecilis, B. thetaiotaomicron* and *B. vulgatus*; (o) *E. faecilis, B. fragilis, B. thetaiotaomicron* and *B. vulgatus*; (p) *Bacteroides* bacteria; (q) *B. fragilis* and *B. thetaiotaomicron*; (r) *B. fragilis,* and *B. vulgatus*; (s) *B. thetaiotaomicron* and *B. vulgatus*; or (t) *B. fragilis, B. thetaiotaomicron* and *B. vulgatus*. Following administration of the bacteria, the vocalization and/or communication behavior can be improved. In some embodiments, the communication behavior in need of improvement (and subsequently improved) comprises at least one of communication, sociability, or language comprehension and/or production. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the *B. fragilis* comprises wild-type *B. fragilis*, mutant *B. fragilis* lacking polysaccharide A (dPSA), or a combination of wild-type *B. fragilis* and dPSA *B. fragilis*. In some embodiments, the subject has communication behavior deficiencies associated with ASD, for example deficient communication, sociability, and language comprehension and/or production. In some embodiments, the subject has sensorimotor gating behavior deficiencies associated with ASD. In some embodiments, the subject has communication behavior deficiencies associated with schizophrenia, for example deficient communication, sociability, and language comprehension and/or production. In some embodiments, the subject has sensorimotor gating behavior deficiencies associated with schizophrenia.

In some embodiments, the subject is in need of improvement in sensorimotor gating and/or communication behavior, and an effective amount of a probiotic comprising, consisting of, or consisting essentially of at least one of the following is provided for administration to the subject (or is for use in treating the subject): (a) *Enterococcus* bacteria (e.g., *E. faecilis, E. faecium, E. hirae, E. avium, E. durans, E. gallinarum,* or *E. casseliflavus*); (b) *Enterococcus* bacteria (e.g., *E. faecilis, E. faecium, E. hirae, E. avium, E. durans, E. gallinarum,* or *E. casseliflavus*); and *Bacteroides* bacteria (e.g., *B. fragilis, B. thetaiotaomicron* or *B. vulgatus*); (c) *Enterococcus* bacteria and *B. fragilis*; (d) *Enterococcus* bacteria and *B. thetaiotaomicron*; (d) *Enterococcus* bacteria and *B. vulgatus*; (e) *Enterococcus* bacteria, *B. fragilis,* and *B. thetaiotaomicron,* (f) *Enterococcus* bacteria, *B. fragilis,* and *B. vulgatus*; (g) *Enterococcus* bacteria, *B. thetaiotaomicron* and *B. vulgatus*; (h) *Enterococcus* bacteria, *B. fragilis, B. thetaiotaomicron* and *B. vulgatus*; (i) *E. faecilis* and *B. fragilis*; (j) *E. faecilis* and *B. thetaiotaomicron*; (k) *E. faecilis* and *B. vulgatus*; (1) *E. faecilis, B. fragilis,* and *B. thetaiotaomicron,* (m) *E. faecilis, B. fragilis,* and *B. vulgatus*; (n) *E. faecilis, B. thetaiotaomicron* and *B. vulgatus*; (o) *E. faecilis, B. fragilis, B. thetaiotaomicron* and *B. vulgatus*; (p) *Bacteroides* bacteria; (q) *B. fragilis* and *B. thetaiotaomicron*; (r) *B. fragilis,* and *B. vulgatus*; (s) *B. thetaiotaomicron* and *B. vulgatus*; or (t) *B. fragilis, B. thetaiotaomicron* and *B. vulgatus*. Following administration of the bacteria, the sensorimotor gating and/or communication behavior can be improved. In some embodiments, the subject is in need of improved sensorimotor gating behavior.

In some embodiments, the subject is in need of improved communication behavior. In some embodiments, the subject is in need of improved sensorimotor gating and communication behavior. In some embodiments, the communication behavior in need of improvement (and subsequently improved) comprises at least one of communication, sociability, or language comprehension and/or language production. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the B. fragilis comprises wild-type B. fragilis, mutant B. fragilis lacking polysaccharide A (dPSA), or a combination of wild-type B. fragilis and dPSA B. fragilis. In some embodiments, the subject is further in need of improvement of defects in intestinal barrier integrity, and following administration of the probiotic, the defects in defects in intestinal barrier integrity are improved. In some embodiments, the subject has communication behavior deficiencies associated with ASD, for example deficient communication, sociability, and language comprehension and/or production. In some embodiments, the subject has sensorimotor gating behavior deficiencies associated with ASD. In some embodiments, the subject has communication behavior deficiencies associated with schizophrenia, for example deficient communication, sociability, and language comprehension and/or production. In some embodiments, the subject has sensorimotor gating behavior deficiencies associated with schizophrenia. In some embodiments, the subject has ASD. In some embodiments, the subject has schizophrenia.

In some embodiments, the subject is in need of improvement in deficits in intestinal barrier integrity, and an effective amount of a probiotic comprising, consisting of, or consisting essentially of at least one of the following is provided for administration to the subject (or is for use in treating the subject): (a) *Bacteroides* bacteria; (b) *B. fragilis* and *B. thetaiotaomicron*; (c) *B. fragilis*, and *B. vulgatus*; (d) *B. thetaiotaomicron* and *B. vulgatus*; or (e) *B. fragilis, B. thetaiotaomicron* and *B. vulgatus*. Following administration of the bacteria, the deficits in intestinal barrier integrity can be improved. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the B. fragilis comprises wild-type B. fragilis, mutant B. fragilis lacking polysaccharide A (dPSA), or a combination of wild-type B. fragilis and dPSA B. fragilis. In some embodiments, the subject has communication behavior deficiencies associated with ASD, for example deficient communication, sociability, and language comprehension and/or production. In some embodiments, the subject has sensorimotor gating behavior deficiencies associated with ASD. In some embodiments, the subject has communication behavior deficiencies associated with schizophrenia, for example deficient communication, sociability, and language comprehension and/or production. In some embodiments, the subject has sensorimotor gating behavior deficiencies associated with schizophrenia. In some embodiments, the subject has defects in intestinal barrier integrity associated with ASD. In some embodiments, the subject has defects in intestinal barrier integrity associated with schizophrenia. In some embodiments, the subject has ASD. In some embodiments, the subject has schizophrenia.

In some embodiments, the subject is in need of improvement in anxiety behavior, and an effective amount of a probiotic comprising, consisting of, or consisting essentially of at least one of the following is provided for administration to the subject (or is for use in treating the subject): (a) *Bacteroides* bacteria; (b) *B. fragilis* and *B. thetaiotaomicron*; (c) *B. fragilis*, and *B. vulgatus*; (d) *B. thetaiotaomicron* and *B. vulgatus*; or (e) *B. fragilis, B. thetaiotaomicron* and *B. vulgatus*. Following administration of the bacteria, the anxiety behavior can be improved. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the B. fragilis comprises wild-type B. fragilis, mutant B. fragilis lacking polysaccharide A (dPSA), or a combination of wild-type B. fragilis and dPSA B. fragilis. In some embodiments, the subject is further in need of improvement of defects in intestinal barrier integrity, and following administration of the probiotic, the defects in defects in intestinal barrier integrity are improved. In some embodiments, the anxiety behavior is associated with ASD or schizophrenia. In some embodiments, the subject has ASD. In some embodiments, the subject has schizophrenia.

In some embodiments, the subject is in need of improvement in repetitive behavior, and an effective amount of a probiotic comprising, consisting of, or consisting essentially of at least one of the following is provided for administration to the subject (or is for use in treating the subject): (a) *Bacteroides* bacteria; (b) *B. fragilis* and *B. thetaiotaomicron*; (c) *B. fragilis*, and *B. vulgatus*; (d) *B. thetaiotaomicron* and *B. vulgatus*; or (e) *B. fragilis, B. thetaiotaomicron* and *B. vulgatus*. Following administration of the bacteria, the repetitive behavior can be improved. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the *B. fragilis* comprises wild-type *B. fragilis*, mutant *B. fragilis* lacking polysaccharide A (dPSA), or a combination of wild-type *B. fragilis* and dPSA *B. fragilis*. In some embodiments, the subject is further in need of improvement of defects in intestinal barrier integrity, and following administration of the probiotic, the defects in defects in intestinal barrier integrity are improved. In some embodiments, the repetitive behavior is associated with ASD or schizophrenia. In some embodiments, the subject has ASD. In some embodiments, the subject has schizophrenia.

In some embodiments, the probiotic comprises any of the above-disclosed bacterial species or combinations of bacterial species, and is provided for administration to the subject (or is for administration to the subject) in a single probiotic composition. In some embodiments, the probiotic comprises any of the above-referenced bacterial species or combinations of bacterial species, and is administered to the subject (or is for administration to the subject) in two or more different probiotic compositions. For example, a probiotic of "bacteria A and bacteria B" can be administered either in a single composition comprising bacteria A and bacteria B, or in a first composition comprising bacteria A in conjunction with a second composition comprising bacteria B. In some embodiments, first and second compositions are administered simultaneously. In some embodiments, the first and second compositions are administered separately.

In some embodiments, a probiotic comprising a combination of *Enterococcus* bacteria and *Bacteroides* bacteria as described herein is provided as a first composition comprising the *Enterococcus* bacteria, and a second composition comprising the *Bacteroides* bacteria or combination of *Bacteroides* bacteria as described herein. In some embodiments, the *Enterococcus* bacteria and at least one *Bacteroides* (or combination of *Bacteroides* bacteria) are administered in a first composition, and at least one different *Bacteroides* bacteria (or different combination of *Bacteroides* bacteria) is administered in a second composition. In some embodiments, the *Enterococcus* bacteria and a first *Bacteroides* bacteria (or combination of *Bacteroides* bacteria) is administered in a first composition, and the *Enterococcus* bacteria and a second *Bacteroides* bacteria (or combination of *Bacteroides* bacteria) that is different from the first is administered in a second composition. In some embodiments, the *Enterococcus* bacteria and a first *Bacteroides* bacteria (or combination of *Bacteroides* bacteria) is administered in a first composition, and a second *Bacteroides* bacteria (or combination of *Bacteroides* bacteria) that is different from the first is administered in a second composition.

In some embodiments, a probiotic comprising a combination of *Bacteroides* bacteria as described herein is administered via a first composition comprising a first *Bacteroides* bacteria or combination of *Bacteroides* bacteria, and a second composition comprising a second *Bacteroides* bacteria or combination of *Bacteroides* bacteria that is different from the first.

In accordance with any of the embodiments described above, optionally, each composition, use or method is free of, or is substantially free of bacteria other than the identified bacteria of the probiotic. In accordance with any of the embodiments above, optionally, each composition is free of, or is substantially free of antibiotics. In accordance with any of the embodiments above, optionally, each composition is free of, or is substantially free of bacteria other than the probiotic and antibiotics.

In accordance with embodiments described herein, the probiotics of the methods, uses, and compositions described herein can be for any suitable route of administration. For example, the probiotic can be administered to the subject via oral administration, rectum administration, transdermal administration, intranasal administration or inhalation. In some embodiments, the probiotic is administered to the subject orally.

In some embodiments, the effective amount of bacteria in the probiotic composition, use, or method includes at least about $10^4$ colony forming units (cfu), for example at least about $10^4$, $10^5$, $10^6$, $10^7$, $10^8$, $10^9$, $10^{10}$, $10^{11}$, $10^{12}$, or $10^{13}$ cfu, including ranges between any of the listed values, for example $10^4$-$10^8$ cfu, $10^4$-$10^9$ cfu, $10^4$-$10^{10}$ cfu, $10^4$-$10^{11}$ cfu, $10^4$-$10^{12}$ cfu, $10^4$-$10^{12}$ cfu, $10^5$-$10^8$ cfu, $10^5$-$10^9$ cfu, $10^5$-$10^{10}$ cfu, $10^5$-$10^{11}$ cfu, $10^5$-$10^{12}$ cfu, $10^5$-$10^{12}$ cfu, $10^6$-$10^8$ cfu, $10^6$-$10^9$ cfu, $10^6$-$10^{10}$ cfu, $10^6$-$10^{11}$ cfu, $10^6$-$10^{12}$ cfu, $10^6$-$10^{12}$ cfu, $10^7$-$10^8$ cfu, $10^7$-$10^9$ cfu, $10^7$-$10^{10}$ cfu, $10^7$-$10^{11}$ cfu, $10^7$-$10^{12}$ cfu, $10^7$-$10^{12}$ cfu,-$10^9$ cfu, $10^8$-$10^{10}$ cfu, $10^8$-$10^{11}$ cfu, $10^8$-$10^{12}$ cfu, or $10^8$-$10^{12}$ cfu. In some embodiments, the effective amount of bacteria comprises a log phase quantity (at 37° C.) of bacteria in a composition for administration to the subject. In some embodiments, the effective amount of bacteria comprises a stationary phase quantity (at 37° C.) of bacteria in a composition for administration to the subject.

Methods of Treating and/or Preventing ASD and/or Schizophrenia Symptoms

In some embodiments, methods of treating ASD and/or schizophrenia symptoms are provided. The method can comprise identifying a subject as in need of improving a sensorimotor gating behavior, and/or communication behavior. The method can comprise administering an effective amount of a probiotic comprising, consisting essentially of, or consisting of *Enterococcus* bacteria, *Bacteroides* bacteria, or a combination of *Enterococcus* bacteria and *Bacteroides* bacteria as described herein is administered to the subject in need of improved sensorimotor gating behavior and/or communication behavior. The subject can exhibit improved sensorimotor gating behavior and/or communication behavior. In some embodiments, the subject is in need of improved sensorimotor gating behavior, and following administration of the probiotic, sensorimotor gating behavior is improved. In some embodiments, the subject is in need of improved communication behavior, and following administration of the probiotic, communication behavior is improved. In some embodiments, the subject is in need of improved communication and sensorimotor gating behavior, and following administration of the probiotic, communication behavior and sensorimotor gating behavior are improved. In some embodiments, the communication behavior in need of improvement (and subsequently improved) comprises at least one of communication, sociability, or language comprehension and/or language production. In some embodiments, the subject has ASD. In some embodiments, the method further comprises determining whether the subject has ASD, and the effective amount of probiotic is administered if the subject has ASD. In some embodiments, the subject has schizophrenia. In some embodiments, the method further comprises determining whether the subject has schizophrenia, and the effective amount of probiotic is administered if the subject has schizophrenia.

In some embodiments, the subject is in need of improved anxiety behavior. The method can comprise identifying the subject as in need of improved anxiety behavior. The method can comprise administering an effective amount of a probiotic comprising, consisting essentially of, or consisting of *Enterococcus* bacteria, *Bacteroides* bacteria, or a combination of *Enterococcus* bacteria and *Bacteroides* bacteria as described herein can be administered to the subject in need of improved anxiety behavior, and following administration of the probiotic, anxiety behavior is improved. In some embodiments, the subject is in need of improved sensorimotor gating behavior and anxiety behavior, and following administration of the probiotic, sensorimotor gating behavior and communication behavior are improved. In some embodiments, the subject is in need of improved communication behavior and anxiety behavior, and following administration of the probiotic, communication behavior and anxiety behavior are improved. In some embodiments, the subject is in need of improved communication behavior, and following administration of the probiotic, communication behavior is improved. In some embodiments, the communication behavior in need of improvement (and subsequently improved) comprises at least one of communication, sociability, or language comprehension and/or language production. In some embodiments, the subject is in need of improved sensorimotor gating behavior, communication behavior, and anxiety behavior, and following administration of the probiotic, sensorimotor gating behavior and anxiety behavior are improved. In some embodiments, the subject is further identified as in need of improvement of defects in intestinal barrier integrity, and following administration of the probiotic, the defects in defects in intestinal barrier integrity are improved. In some embodiments, the subject has ASD. In some embodiments, the method further comprises determining whether the subject has ASD, and the effective amount of probiotic is administered if the subject has ASD. In some embodiments, the subject has schizophrenia. In some embodiments, the method further comprises determining whether the subject has schizophrenia, and the effective amount of probiotic is administered if the subject has schizophrenia.

In some embodiments, methods of treating ASD or schizophrenia symptoms are provided. The method can comprise identifying the subject as in need of improving sensorimotor gating behavior. The method can comprise administering an effective amount of a probiotic comprising, consisting essentially of, or consisting of *Enterococcus* bacteria, *Bacteroides* bacteria, or a combination of *Enterococcus* bacteria and *Bacteroides* bacteria as described herein is administered to the subject. Following administration of the probiotic, sensorimotor gating behavior in the subject can be improved. In some embodiments, the subject is further identified as in need of improvement of defects in intestinal barrier integrity, and following administration of the probiotic, the defects in defects in intestinal barrier integrity are improved. In some embodiments, the subject has ASD. In some embodiments, the method further comprises determining whether the subject has ASD, and the effective amount of probiotic is administered if the subject has ASD. In some embodiments, the subject has schizophrenia. In some embodiments, the method further comprises determining whether the subject has schizophrenia, and the effective amount of probiotic is administered if the subject has schizophrenia.

In some embodiments, methods of treating ASD or schizophrenia symptoms are provided. The method can comprise identifying the subject as in need of improving communication behavior. The method can comprise administering an effective amount of a probiotic comprising, consisting essentially of, or consisting of *Enterococcus* bacteria, *Bacteroides* bacteria, or a combination of *Enterococcus* bacteria and *Bacteroides* bacteria as described herein to the subject. Following administration of the probiotic, communication behavior in the subject can be improved. In some embodiments, the communication behavior in need of improvement (and subsequently improved) comprises at least one of communication, sociability, or language comprehension and/or language production. In some embodiments, the subject is further identified as in need of improvement of defects in intestinal barrier integrity, and following administration of the probiotic, the defects in defects in intestinal barrier integrity are improved.

In some embodiments, methods of treating ASD or schizophrenia symptoms are provided. The method can comprise identifying the subject as in need of improving sensorimotor gating and communication behavior. The method can comprise administering a probiotic comprising, consisting essentially of, or consisting of an effective amount of *Enterococcus* bacteria, *Bacteroides* bacteria, or a combination of *Enterococcus* bacteria and *Bacteroides* bacteria as described herein to the subject. Following acute administration of the probiotic, sensorimotor and communication behavior in the subject can be improved. In some embodiments, the communication behavior in need of improvement (and subsequently improved after administration of the probiotic) comprises at least one of communication, sociability, or language comprehension and/or language production. In some embodiments, the subject is further identified as in need of improvement of defects in intestinal barrier integrity, and following administration of the probiotic, the defects in defects in intestinal barrier integrity are improved.

In some embodiments, methods of ameliorating symptoms of ASD or schizophrenia are provided. The method can comprise identifying the subject as having gastrointestinal or immunological abnormalities or pathologies associated with ASD or schizophrenia. The method can comprise administering a probiotic comprising, consisting essentially of, or consisting of an effective amount of *Enterococcus* bacteria, *Bacteroides* bacteria, or a combination of *Enterococcus* bacteria and *Bacteroides* bacteria as described herein can be administered to the subject. Following acute administration of the probiotic, the ASD or schizophrenia symptoms can be ameliorated. In some embodiments, the subject is identified as having ASD or schizophrenia symptoms that comprise gastrointestinal abnormalities associated with ASD or schizophrenia, and these symptoms are improved following administration of the probiotic. In some embodiments, the subject is identified as having ASD or schizophrenia symptoms that comprise immunological abnormalities associated with ASD or schizophrenia, and these symptoms are improved following administration of the probiotic. In some embodiments, the subject is identified as having ASD or schizophrenia symptoms that comprise immunological and gastrointestinal abnormalities associated with ASD or schizophrenia, and these symptoms are improved following administration of the probiotic. In some embodiments, the subject is identified as having ASD symptoms that comprise gastrointestinal abnormalities associated with ASD, and these symptoms are improved following administration of the probiotic. In some embodiments, the subject is identified as having ASD symptoms that comprise immunological abnormalities associated with ASD, and these symptoms are improved following administration of the probiotic. In some embodiments, the subject is identified as having ASD symptoms that comprise immunological and gastrointestinal abnormalities associated with ASD, and these symptoms are improved following administration of the probiotic. In some embodiments, the subject is identified as having schizophrenia symptoms that comprise gastrointestinal abnormalities associated with schizophrenia, and these symptoms are improved following administration of the probiotic. In some embodiments, the subject is identified as having schizophrenia symptoms that comprise immunological abnormalities associated with schizophrenia, and these symptoms are improved following administration of the probiotic. In some embodiments, the subject is identified as having schizophrenia symptoms that comprise immunological and gastrointestinal abnormalities associated with schizophrenia, and these symptoms are improved following administration of the probiotic. In some embodiments, the subject is further identified as in need or improving sensorimotor gating, communication, anxiety, and or repetitive behavior, and following administration of the probiotic, the corresponding sensorimotor gating, communication, anxiety, and or repetitive behavior(s) are improved.

In some embodiments, methods of treating ASD or schizophrenia symptoms are provided. The method can comprise identifying the subject as being in need of improving repetitive behavior. The method can comprise administering a probiotic comprising, consisting essentially of, or consisting of an effective amount of *Enterococcus* bacteria, *Bacteroides* bacteria, or a combination of *Enterococcus* bacteria and *Bacteroides* bacteria as described herein is administered to the subject. Following acute administration of the probiotic, repetitive behavior in the subject can be improved.

In some embodiments, methods of preventing ASD or schizophrenia symptoms are provided. The method can comprise identifying the subject as at risk for developing a sensorimotor gating behavior deficiency. The method can comprise administering an effective amount of a probiotic comprising, consisting essentially of, or consisting of *Enterococcus* bacteria, *Bacteroides* bacteria, or a combination of *Enterococcus* bacteria and *Bacteroides* bacteria as described herein to the subject in need of behavioral improvement. The subject can develop with minimized deficiencies or no discernable deficiencies in sensorimotor behavior. In some embodiments, the ASD or schizophrenia symptoms further comprise at least one of: impaired communication behavior, anxiety behavior, or repetitive behavior, and following administration of the probiotic the subject develops with minimized deficiencies or no discernable deficiencies in the respective impaired communication behavior, anxiety behavior, or repetitive behavior. In some embodiments, the at-risk subject is an infant or child.

In some embodiments, methods of preventing ASD, or schizophrenia symptoms are provided. The method can comprise identifying a subject as at risk for developing a communication behavior deficiency. The method can comprise administering an effective amount of a probiotic comprising, consisting essentially of, or consisting of *Enterococcus* bacteria, *Bacteroides* bacteria, or a combination of *Enterococcus* bacteria and *Bacteroides* bacteria as described herein is administered to the subject in need of behavioral improvement. The subject can develop with minimized deficiencies or no discernable deficiencies in communication behavior. In some embodiments, the communication behavior in need of improvement (and subsequently improved after administration of the probiotic) comprises at least one of communication, sociability, or language comprehension and/or language production. In some embodiments, the ASD or schizophrenia symptoms further comprise at least one of: impaired sensorimotor gating behavior, anxiety behavior, or repetitive behavior, and following administration of the probiotic the subject develops with minimized deficiencies or no discernable deficiencies in sensorimotor gating behavior, anxiety behavior, or repetitive behavior is improved. In some embodiments, the at-risk subject is an infant or child.

In some embodiments, methods of preventing ASD symptoms are provided. The method can comprise identifying a subject as at risk for developing a communication behavior deficiency and sensory gating behavior deficiency. The method can comprise administering an effective amount of a probiotic comprising, consisting essentially of, or consisting of *Enterococcus* bacteria, *Bacteroides* bacteria, or a combination of *Enterococcus* bacteria and *Bacteroides* bacteria as described herein is administered to the subject at risk. The subject can develop with minimized deficiencies or no discernable deficiencies in social communication behavior. In some embodiments, the communication behavior comprises at least one of communication, sociability, or language comprehension and/or language production. Optionally, the at-risk subject is an infant or child.

In some embodiments, for any of the above methods, the probiotic comprising, consisting essentially of, or consisting of *Enterococcus* bacteria, *Bacteroides* bacteria, or a combination of *Enterococcus* bacteria and *Bacteroides* bacteria of any of the methods described herein is selected from the group consisting of: (a) *Enterococcus* bacteria (e.g., *E. faecilis, E. faecium, E. hirae, E. avium, E.E. durans, E. gallinarum*, or *E. casseliflavus*); (b) *Enterococcus* bacteria (e.g., *E. faecilis, E. faecium, E. hirae, E. avium, E. durans, E. gallinarum*, or *E. casseliflavus*); and *Bacteroides* bacteria (e.g., *B. fragilis, B. thetaiotaomicron* or *B. vulgatus*); (c) *Enterococcus* bacteria and *B. fragilis*; (d) *Enterococcus* bacteria and *B. thetaiotaomicron*; (d) *Enterococcus* bacteria and *B. vulgatus*; (e) *Enterococcus* bacteria, *B. fragilis*, and *B. thetaiotaomicron*, (f) *Enterococcus* bacteria, *B. fragilis*, and *B. vulgatus*; (g) *Enterococcus* bacteria, *B. thetaiotaomicron* and *B. vulgatus*; (h) *Enterococcus* bacteria, *B. fragilis, B. thetaiotaomicron* and *B. vulgatus*; (i) *E. faecilis* and *B. fragilis*; (j) *E. faecilis* and *B. thetaiotaomicron*; (k) *E. faecilis* and *B. vulgatus*; (l) *E. faecilis, B. fragilis*, and *B. thetaiotaomicron*, (m) *E. faecilis, B. fragilis*, and *B. vulgatus*; (n) *E. faecilis, B. thetaiotaomicron* and *B. vulgatus*; (o) *E. faecilis, B. fragilis, B. thetaiotaomicron* and *B. vulgatus*; (p) *Bacteroides* bacteria; (q) *B. fragilis* and *B. thetaiotaomicron*; (r) *B. fragilis*, and *B. vulgatus*; (s) *B. thetaiotaomicron* and *B. vulgatus*; or (t) *B. fragilis, B. thetaiotaomicron* and *B. vulgatus*. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients.

In some embodiments as described above, the method further comprises determining that the subject is in need of improving a behavior. In some embodiments, for example uses, methods, and or compositions directed to infants and/or children, a subject at risk for an ASD behavior is identified based on maternal immune activation and/or other risk factors. In some embodiments, the subject is diagnosed as having ASD based on the level of an ASD-related metabolite or combination of metabolites in the gut, in a bodily fluid (for example, blood and urine), or any combination thereof. Methods of diagnosing ASD based on levels of metabolite in a subject are described in detail in US Pub. No. 2014/0065132, hereby incorporated by reference in its entirety. In some embodiments, the subject is determined to have a lesion or developmental deficiency in a region of the brain associated with speech production, speech recognition, impulse control, and socialization, for example regions of the cerebral cortex, the corpus colosum, Broca's area, and/or Wernicke's area. In some embodiments, an ASD behavior, for example a deficient communication, vocalization, sensorimotor, anxiety, and/or repetitive behavior, or a combination of two or more of these is identified using standard diagnostic criteria, for example in the Diagnostic and Statistical Manual of Mental Disorders, Fourth Edition (DSM-4) or Fifth Edition (DSM-5). In some embodiments, the presence or absence of ASD in the subject is determined using a behavioral test, for example at least one of the Autism Behavior Checklist (ABC), Autism diagnostic Interview-Revised (ADI-R), childhood autism Rating Scale (CARS), and/or Pre-Linguistic Autism Diagnostic Observation Schedule (PL-ADOS). The behavioral test can include, but is not limited to, detecting the presence and/or extent of 1) preoccupation with one or more stereotyped and restricted patterns of interest that is abnormal in either intensity or focus, 2) inflexible adherence to specific, nonfunctional routines or rituals, c) stereotyped and repetitive motor mannerisms (such as hand flapping, finger flapping etc.), and/or d) persistent preoccupation with parts of objects. Non-limiting examples of behavior that can be included in a behavioral test and suggest a need for improving behavioral performance in the subject under the test include: a) sensory behaviors, including poor use of visual discrimination when learning, seems not to hear, so that a hearing loss is suspected, sometimes shows no "startle response" to loud noise", sometimes painful stimuli such as bruises, cuts, and injections evoke no reaction, often will not blink when bright light is directed toward eyes, covers ears at many sounds, squints, frowns, or covers eyes when in the presence of natural light, frequently has no visual reaction to a "new" person, stares into space for long periods of time; b) relating behaviors: frequently does not attend to social/environmental stimuli, has no social smile, does not reach out when reached for, non-responsive to other people's facial expressions/feelings, actively avoids eye contact, resists being touched or held, is flaccid when held in arms, is stiff and hard to held, does not imitate other children at play, has not developed any friendships, often frightened or very anxious, "looks through" people; c) body and object use behaviors: whirls self for long periods of time, does not use toys appropriately, insists on keeping certain objects with him/her, rocks self for long periods of time, does a lot of lunging and darting, flaps hands, walks on toes, hurts self by banging head, biting hand, twirls, spins, and bangs objects a lot, feel, smell, and/or taste objects in the environment, gets involved in complicated "rituals" such as lining things up, is very destructive; and d) language behaviors: does not follow simple commands given once, has pronoun reversal, speech is atonal, does not respond to own name when called out among two others, seldom says "yes" or "I", does not follow simple commands involving prepositions, gets desired objects by gesturing, repeats phrases over and over, cannot point to more than five named objects, uses 0-5 spontaneous words per day to communicate wants and needs, repeats sounds or words over and over, echoes questions or statements made by others, uses at least 15 but less than 30 spontaneous phrases daily to communicate, learns a simple task but "forgets" quickly, strong reactions to changes in routine/environment, has "special abilities" in one area of development, which seems to rule out mental retardation, severe temper tantrums and/or frequent minor tantrums, hurts others by biting, hitting, and/or kicking, does not wait for needs to be met, difficulties with toileting, does not dress self without frequent help, frequently unaware of surroundings, and may be oblivious to dangerous situations, prefers to manipulate and be occupied with inanimate things, and/or a developmental delay identified at or before 30 months of age. One of ordinary skill in the art would appreciate that the attending physician would know how to identify a subject in need of treatment disclosed herein.

In some embodiments as described above, the method comprises administering the effective amount of probiotic in a single administration of one or more compositions. In some embodiments as described above, the method comprises administering the effective amount of the probiotic across two or more administrations of a single composition as described herein. For example, the compositions can be administered about 1 minute, 2, 3, 4, 5, 6, 7, 8, 9, 10, 15, 20, 25, 30, 35, 40, 45, 50, 55 minutes, 1 hour, 2, 3, 4, 5, 6, 7, 8, 9, 10, 11, 12, 13, 14, 15, 16, 17, 18, 19, 20, 21, 22, 23 hours, 1 day, 2, 3, 4, 5, 6, 7, 8, 9, or 10 days apart, including ranges between any two of the listed values, for example 1 minute-10 minutes, 1 minute to 30 minutes, 1 minute to 1 hour, 1 minute-2 hours, 1 minute-4 hours, 1 minute-12 hours, 1 minute-18 hours, 1 minute-1 day, 10 minutes to 30 minutes, 10 minutes to 1 hour, 10 minutes-2 hours, 10 minutes-4 hours, 10 minute-12 hours, 10 minutes-18 hours, 10 minutes-1 day, 30 minutes to 1 hour, 30 minutes-2 hours, 30 minutes-4 hours, 30 minute-12 hours, 30 minutes-18 hours, 30 minutes-1 day, 30 minutes-2 days, 1 hour-2 hours, 1 hour-4 hours, 1 hour-12 hours, 1 hour-18 hours, 1 hour-1 day, 4 hours-12 hours, 4 hours-18 hours, 4 hours-1 day, 1 day-2 days, 1 day-3 days, 1 day-4 days, 1 day-5 days, 1 day-7 days, 1 day-10 days, 2 days-3 days, 2 days-4 days, 2 days-5 days, 2 days-7 days, 2 days-10 days, or 5 days to 10 days. In some embodiments as described above, the method comprises administering the effective amount of two or more different compositions as described herein across two or more administrations of a single composition. For example, the second composition can be administered about 1 minute, 2, 3, 4, 5, 6, 7, 8, 9, 10, 15, 20, 25, 30, 35, 40, 45, 50, 55 minutes, 1 hour, 2, 3, 4, 5, 6, 7, 8, 9, 10, 11, 12, 13, 14, 15, 16, 17, 18, 19, 20, 21, 22, 23 hours, 1 day, 2, 3, 4, 5, 6, 7, 8, 9, or 10 days after the first composition, including ranges between any two of the listed values, for example 1 minute-10 minutes, 1 minute to 30 minutes, 1 minute to 1 hour, 1 minute-2 hours, 1 minute-4 hours, 1 minute*12 hours, 1 minute-18 hours, 1 minute-1 day, 10 minutes to 30 minutes, 10 minutes to 1 hour, 10 minutes-2 hours, 10 minutes-4 hours, 10 minute-12 hours, 10 minutes-18 hours, 10 minutes-1 day, 30 minutes to 1 hour, 30 minutes-2 hours, 30 minutes-4 hours, 30 minute-12 hours, 30 minutes-18 hours, 30 minutes-1 day, 30 minutes-2 days, 1 hour-2 hours, 1 hour-4 hours, 1 hour-12 hours, 1 hour-18 hours, 1 hour-1 day, 4 hours-12 hours, 4 hours-18 hours, 4 hours-1 day, 1 day-2 days, 1 day-3 days, 1 day-4 days, 1 day-5 days, 1 day-7 days, 1 day-10 days, 2 days-3 days, 2 days-4 days, 2 days-5 days, 2 days-7 days, 2 days-10 days, or 5 days to 10 days. In some embodiments, the probiotic is administered in a slow release formulation (for example a slow-release capsule or implant) for any of the durations described above.

In some embodiments, the probiotic is administered to the subject until an improvement in behavioral performance is observed. Optionally, the probiotic is administered to the subject after an improvement in behavioral performance is observed, for example to solidify or maintain the improved behavioral performance.

EXAMPLES

Some aspects of the embodiments discussed above are disclosed in further detail in the following examples, which are not in any way intended to limit the scope of the present disclosure.

Example 1: Acute Postnatal Treatment with *B. fragilis*, dPSA *B. fragilis*, and *B. vulgatus*, but not *E. faecalis* Corrects Defects in Intestinal Barrier Integrity in the MIA Mouse Model for Autism Offspring of immune-activated mothers were given applesauce containing each bacterium or applesauce alone for 1 week post-weaning. 6 weeks after bacterial treatment, mice were orally gavaged with FITC-dextran to measure intestinal permeability in vivo, alongside a positive control or a chemically-induced colitis mouse model. Poly(I:C) was administered as an immune activator in mothers. The results are shown in FIG. 1. Treatment with *B. fragilis* (n=9), *B. thetaiotaomicron* (n=7), and *B. vulgatus*(n=5) significantly reduced leakage of FITC-dextran into the bloodstream in the MIA mouse model for autism. *E. faecalis* (n=6) treatment had no significant effect.

Thus, acute postnatal treatment with *B. fragilis*, mutant *B. fragilis* lacking polysaccharide A (dPSA), *B. thetaiotaomicron*, and *B. vulgatus*, but not *E. faecalis* corrects defects in intestinal barrier integrity in the MIA mouse model for autism in accordance with some embodiments described herein.

Example 2: Acute Postnatal Treatment with *B. fragilis*, dPSA *B. fragilis, B. thetaiotaomicron*, and *B. vulgatus*, but not *E. faecalis* Corrects Anxiety-Like Behaviors in the MIA Mouse Model for Autism Offspring of immune-activated mothers were given applesauce containing each bacterium or applesauce alone for 1 week post-weaning. Poly(I:C) was administered as an immune activator in mothers. 3-6 weeks after bacterial treatment, mice were tested for anxiety-like and exploratory behavior in the open field exploration task. Treatment with *B. fragilis* (n=47), *B. thetaiotaomicron* (n=32), and *B. vulgatus* (n=20) reduced anxiety-like behavior in the MIA mouse model for autism, as measured by increased entries into the center of the open area (FIG. 2A), and increased duration spent in the center of the open area (FIG. 2B). *E. faecalis* (n=16) treatment had no significant effect in either of these assays.

Thus, acute postnatal treatment with *B. fragilis*, mutant *B. fragilis* lacking polysaccharide A (dPSA), *B. thetaiotaomicron*, and *B. vulgatus*, but not *E. faecalis* corrects anxiety-like behaviors in the MIA mouse model for autism in accordance with some embodiments described herein.

Example 3: Acute Postnatal Treatment with *B. fragilis*, dPSA *B. fragilis, B. thetaiotaomicron*, and *B. vulgatus*, but not *E. faecalis* Improves Repetitive Behaviors in the MIA Mouse Model for Autism Offspring of immune-activated mothers were given applesauce containing each bacterium or applesauce alone for 1 week post-weaning. 3-6 weeks after bacterial treatment, mice were tested for repetitive behavior in the stereotyped marble burying task. Treatment with *B. fragilis* (n=30), *B. thetaiotaomicron* (n=32), and *B. vulgatus* (n=18) reduced compulsive marble burying in the MIA mouse model for autism. *E faecalis* (n=16) had no apparent effect in this assay.

Thus, acute postnatal treatment with *B. fragilis*, mutant *B. fragilis* lacking polysaccharide A (dPSA), *B. thetaiotaomicron*, and *B. vulgatus*, but not *E. faecalis* improves repetitive behaviors in the maternal immune activation (MIA) mouse model for autism in accordance with some embodiments described herein.

Example 4: Acute Postnatal Treatment with *B. fragilis, B. thetaiotaomicron, B. vulgatus*, and *E. faecalis* Improves Communicative Behavior in the MIA Mouse Model for Autism Offspring of immune-activated mothers were given applesauce containing each bacterium or applesauce alone for 1 week post-weaning. 3-6 weeks after bacterial treatment, mice were tested for ultrasonic vocalizations in response to exposure to unfamiliar female stimulus mouse. Treatment with *B. fragilis* (n=10), *B. thetaiotaomicron* (n=10), and *B. vulgatus*(n=10) and *E. faecalis* (n=10) significantly increased the total number of calls produced (see FIG. 4A), significantly increased average duration per call (see FIG. 4B), and significantly increased total duration of vocalization (see FIG. 4C) in the MIA mouse model of autism. Mutant *B. fragilis* lacking polysaccharide A (dPSA) treatment has no significant effect.

Thus, acute postnatal treatment with *B. fragilis, B. thetaiotaomicron, B. vulgatus*, and *E. faecalis* improves communicative behavior (e.g. total number of calls, average call duration, and total call duration) in the MIA mouse model in accordance with some embodiments described herein.

Example 5: Acute Postnatal Treatment with *B. fragilis, B. thetaiotaomicron*, and *E. faecalis* Improves Sensorimotor Behavior in the MIA Mouse Model for Autism Offspring of immune-activated mothers were given applesauce containing each bacterium or applesauce alone for 1 week post-weaning. 3-6 weeks after bacterial treatment, mice were tested for sensorimotor behavior in the pre-pulse inhibition task. As shown in FIG. 5, Treatment with *B. fragilis* (n=40), *B. thetaiotaomicron* (n=32), and *E. faecalis* (n=16) elevate pre-pulse inhibition in response to a 5 decibel (PP15) and 15 decibel (PPI15) pre-pulse. *B. vulgatus* (n=20) treatment has no apparent effect in this assay.

As shown in FIG. 5, statistically significant differences are observed for a number of bacteria in accordance with some embodiments described herein, as summarized in Table 5. Sensorimotor behavior as measured by % PPI was compared for various treatments. In Table 5, $p<0.05$ is denoted with a single asterisk (*), and $p<0.01$ is denoted with a double asterisk (**).

TABLE 5

| | |
|---|---|
| Saline vs saline B. frag: | 0.0059** |
| Saline vs polyIC | 0.0100* |
| Saline vs polyIC B. frag: | 0.92776 |
| Saline vs polyIC B frag dPSA | 0.1074 |
| Saline vs polyIC B. vulgatus | 0.1415 |
| polyIC vs polyIC B. frag | 0.0189 |
| polyIC vs polyIC B. frag dPSA | 0.8173 |
| polyIC vs polyIC B. theta | 0.0062** |
| polyIC vs polyIC B. vulgatus | 0.6763 |
| polyIC vs polyIC E. faecalis | 0.0712 |

Thus, acute postnatal treatment with *B. fragilis, B. thetaiotaomicron*, and *E. faecalis* improves sensorimotor behavior in the MIA mouse model for autism in accordance with some embodiments described herein.

Example 6: Treatment with *E. faecalis* Improves Sensorimotor Behavior in a Human Exhibiting Sensorimotor Deficiencies A human child subject is identified as having ASD based on the childhood autism Rating Scale (CARS), and exhibits limited sensorimotor response to auditory stimuli. The subject drinks a yogurt comprising an effective amount of a probiotic consisting essentially of *E. faecalis* weekly for three weeks. After about three weeks of drinking the yogurt, the subject is expected to exhibit increased response to auditory stimuli.

Example 7: Treatment with *E. faecalis* Improves Vocalization and Communication Behavior in a Human Exhibiting Vocalization and Communication Deficiencies A human ASD adult subject exhibits limited verbalization and communication behavior in response to verbal prompts from others. The subject swallows a gel capsule comprising an effective amount of a probiotic comprising *E. faecalis* and substantially free of other bacteria and antibiotics daily until the subject exhibits increased verbalization and communication behavior in response to verbal prompts from others.

Example 8: Treatment with *B. thetaiotaomicron* and *E. faecalis* Improves Communication Behavior and Anxiety Behavior in a Human Exhibiting Communication and Anxiety Deficiencies A human ASD adolescent subject exhibits deficient communication and anxiety behaviors. The subject is fed a first yogurt beverage comprising an effective amount of *B. thetaiotaomicron* and a second yogurt beverage comprising an effective amount of *E. faecalis* once every four days. The administration continues on this schedule for eight weeks. After eight weeks, the subject is expected to exhibit improved communication and anxiety behaviors.

Example 9: Acute Postnatal Treatment with *E. faecalis* Improves Sensorimotor and Communication Behavior and Anxiety Behavior in a Human Exhibiting Communication and Anxiety Deficiencies A human infant subject at risk for ASD sensorimotor and communication behavior deficiencies is fed a composition comprising applesauce and an effective amount of *E. faecalis* in a weekly doses post-weaning for ten weeks. The subject is expected to develop without ASD-like sensorimotor and communication behaviors.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those of skill in the art. The various aspects and embodiments disclosed herein are for purposes of illustration and are not intended to be limiting, with the true scope and spirit being indicated by the following claims.

What is claimed is:

1. A method for improving a sensorimotor gating performance in a subject in need thereof, the method comprising:
   selecting a subject having autism spectrum disorder symptoms or schizophrenia symptoms, and in need of improving sensorimotor gating performance; and
   administering to the selected subject a probiotic composition comprising *Enterococcus faecalis* bacteria,
   thereby improving the sensorimotor gating performance in the selected subject.

2. The method of claim 1, wherein the subject suffers from anxiety, autism spectrum disorder (ASD), schizophrenia, or a gastrointestinal or immunological pathology associated with one or more of the symptoms of ASD.

3. The method of claim 1, wherein the subject is further in need of improving a communication behavior.

4. The method of claim 3, wherein the communication behavior in need of improvement comprises at least one of impaired sociability, impaired language comprehension, impaired language production, or impaired communication.

5. The method of claim 1, wherein the probiotic composition administered to the subject in the method consists essentially of the *Enterococcus faecalis* bacteria.

6. The method of claim 1, wherein the probiotic composition is free of bacteria other than the *Enterococcus faecalis* bacteria.

7. The method of claim 1, wherein the probiotic composition administered to the subject in the method is free of drugs and antibiotics.

8. The method of claim 1, further comprising administering one or more *Bacteroides* bacteria to the subject, wherein the one or more *Bacteroides* bacteria are administered in the probiotic composition comprising the *Enterococcus faecalis* bacteria, or wherein the one or more *Bacteroides* are administered in a different probiotic composition than the probiotic composition comprising the *Enterococcus faecalis* bacteria,
   wherein the one or more *Bacteroides* bacteria are selected from the group consisting of: *B. fragilis*, *B. thetaiotaomicron*, and a mixture thereof.

9. The method of claim 3, further comprising administering one or more *Bacteroides* bacteria to the subject, wherein the one or more *Bacteroides* bacteria are administered in the probiotic composition comprising the *Enterococcus faecalis* bacteria, or wherein the *Bacteroides* are administered in a different probiotic composition than the probiotic composition comprising the *Enterococcus faecalis* bacteria,
   wherein the one or more *Bacteroides* bacteria are selected from the group consisting of *B. thetaiotaomicron*, *B. vulgatus*, *B. fragilis*, and a mixture thereof.

10. The method of claim 8, wherein the *Bacteroides* bacteria are administered in the probiotic composition comprising the *Enterococcus faecalis* bacteria.

11. The method of claim 8, wherein the *Bacteroides* are administered in the different probiotic composition than the probiotic composition comprising the *Enterococcus faecalis* bacteria.

12. The method of claim 9, wherein the probiotic composition administered to the subject in the method consists essentially of:
   a mixture of *Enterococcus faecalis* bacteria and *B. fragilis*;
   a mixture of *Enterococcus faecalis* bacteria and *B. thetaiotaomicron*;
   a mixture of *Enterococcus faecalis* bacteria and *B. vulgatus*;
   a mixture of *Enterococcus faecalis* bacteria, *B. fragilis*, and *B. thetaiotaomicron*;
   a mixture of *Enterococcus faecalis* bacteria, *B. fragilis*, and *B. vulgatus*;
   a mixture of *Enterococcus faecalis* bacteria, *B. thetaiotaomicron*, and *B. vulgatus*; or
   a mixture of *Enterococcus faecalis* bacteria, *B. fragilis*, *B. thetaiotaomicron*, and *B. vulgatus*.

13. The method of claim 11, wherein the probiotic composition comprising the *Enterococcus faecalis* bacteria is administered separately from the different probiotic composition comprising one or more *Bacteroides* bacteria, and
   wherein the probiotic composition comprising the *Enterococcus faecalis* bacteria is substantially free of bacteria other than the *Enterococcus faecalis* bacteria, and
   wherein the different probiotic composition comprising the one or more *Bacteroides* bacteria is substantially free of bacteria other than the one or more *Bacteroides* bacteria.

14. The method of claim 1, wherein the probiotic composition comprising the *Enterococcus faecalis* bacteria is effective when administered in combination with a *Bacteroides* bacteria selected from the group consisting of *B. fragilis, B. thetaiotaomicron*, and a mixture thereof.

15. A method for improving sensorimotor gating performance in a subject in need thereof, the method comprising:
    selecting a subject having autism spectrum disorder symptoms or schizophrenia symptoms, and in need of improving sensorimotor gating performance; and
    administering to the selected subject a composition comprising *Enterococcus faecalis* bacteria and *Bacteroides* bacteria, wherein the *Bacteroides* bacteria is selected from the group consisting of: *B. fragilis, B. thetaiomicron*, and a mixture thereof, wherein the composition is substantially free of bacteria other than the *Enterococcus faecalis* and the *Bacteroides* bacteria,
    thereby improving sensorimotor gating performance in the selected subject.

16. The method of claim 9, wherein the *Bacteroides* bacteria are administered in the probiotic composition comprising the *Enterococcus faecalis* bacteria.

17. The method of claim 9, wherein the *Bacteroides* are administered in the different probiotic composition than the probiotic composition comprising the *Enterococcus faecalis* bacteria.

18. The method of claim 8, wherein the one or more *Bacteroides* bacteria is *B. fragilis*.

19. The method of claim 9, wherein the one or more *Bacteroides* bacteria is *B. fragilis*.

* * * * *